(12) United States Patent  
Bartlett et al.

(10) Patent No.: US 8,716,650 B2
(45) Date of Patent: May 6, 2014

(54) NUCLEAR GAUGES AND RELATED METHODS OF ASSEMBLY

(75) Inventors: James E. Bartlett, Cary, NC (US); Raffaello Verna, Creedmoor, NC (US); Donald E. Weger, Wendell, NC (US); Dirk M. Steckmann, Cary, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 753 days.

(21) Appl. No.: 12/348,784

(22) Filed: Jan. 5, 2009

(65) Prior Publication Data

US 2009/0274275 A1 Nov. 5, 2009

Related U.S. Application Data

(60) Provisional application No. 61/010,103, filed on Jan. 4, 2008, provisional application No. 61/010,022, filed on Jan. 4, 2008, provisional application No. 61/010,191, filed on Jan. 4, 2008.

(51) Int. Cl.  
*G12B 13/00* (2006.01)

(52) U.S. Cl.  
USPC .................................................... 250/252.1

(58) Field of Classification Search  
USPC .................................................... 250/252.1  
See application file for complete search history.

(56) References Cited

U.S. PATENT DOCUMENTS

| | | | |
|---|---|---|---|
| 3,544,793 A | 12/1970 | Bless et al. | |
| 3,635,082 A | 1/1972 | Prellwitz et al. | |
| 3,794,843 A | 2/1974 | Chen | |
| 4,219,776 A | 8/1980 | Arulanandan | |
| 4,419,585 A | 12/1983 | Strauss et al. | |
| 4,442,701 A | 4/1984 | Cowherd et al. | |
| 4,525,854 A | 6/1985 | Molbert et al. | |
| 4,587,623 A | 5/1986 | Regimand et al. | |
| 4,641,030 A | 2/1987 | Regimand | |
| 4,701,868 A * | 10/1987 | Regimand | 702/137 |
| 4,749,858 A * | 6/1988 | Young | 250/253 |
| 4,766,319 A | 8/1988 | Regimand | |
| 4,791,656 A | 12/1988 | Pratt, Jr. et al. | |
| 4,904,942 A | 2/1990 | Thompson | |

(Continued)

FOREIGN PATENT DOCUMENTS

CN ZL 200680040215 9/2011  
EP 1 932 020 6/2008

(Continued)

OTHER PUBLICATIONS

Non-Final Official Action for U.S. Appl. No. 13/414,680 (May 30, 2012).

(Continued)

*Primary Examiner* — Christine Sung  
(74) *Attorney, Agent, or Firm* — Jenkins, Wilson, Taylor & Hunt, P.A.

(57) ABSTRACT

Nuclear gauges, their components and method for assembly and adjustment of the same are provided. The nuclear gauges are used in measuring the density and/or moisture of construction-related materials. The nuclear gauge can include a gauge housing having a vertical cavity therethrough and at least one radiation detector located within the housing. The nuclear gauge can include a vertically moveable source rod and a radiation source operatively positioned within a distal end of the source rod.

48 Claims, 29 Drawing Sheets

(56) References Cited

U.S. PATENT DOCUMENTS

| | | | |
|---|---|---|---|
| 5,095,465 | A | 3/1992 | Stokoe, II |
| 5,333,502 | A | 8/1994 | Clark, Jr. et al. |
| 5,457,628 | A | 10/1995 | Theyanayagam |
| H1561 | H | 7/1996 | Thompson |
| 5,614,670 | A | 3/1997 | Nazarian et al. |
| 5,900,736 | A | 5/1999 | Sovik et al. |
| 5,923,726 | A | 7/1999 | Regimand |
| 6,050,725 | A | 4/2000 | Regimand |
| 6,272,434 | B1 | 8/2001 | Wisler et al. |
| 6,310,936 | B1 | 10/2001 | Troxler et al. |
| 6,369,381 | B1* | 4/2002 | Troxler et al. ............ 250/252.1 |
| 6,382,045 | B1 | 5/2002 | Wheeler |
| 6,393,921 | B1 | 5/2002 | Grimes et al. |
| 6,397,661 | B1 | 6/2002 | Grimes et al. |
| 6,400,161 | B1 | 6/2002 | Geisel |
| 6,411,087 | B1 | 6/2002 | Fan et al. |
| 6,414,497 | B1 | 7/2002 | Sovik et al. |
| 6,427,774 | B2 | 8/2002 | Thomas et al. |
| 6,442,232 | B2 | 8/2002 | Troxler et al. |
| 6,567,498 | B1 | 5/2003 | Troxler et al. |
| 6,604,432 | B1 | 8/2003 | Hamblen et al. |
| 6,677,763 | B2 | 1/2004 | Geisel |
| 6,803,771 | B2 | 10/2004 | Sovik et al. |
| 6,823,736 | B1 | 11/2004 | Brock et al. |
| 6,915,216 | B2 | 7/2005 | Troxler et al. |
| RE38,910 | E | 12/2005 | Troxler et al. |
| 6,980,929 | B2 | 12/2005 | Aronstam et al. |
| 7,040,145 | B2 | 5/2006 | Drnevich et al. |
| 7,042,801 | B1 | 5/2006 | Berg |
| 7,107,159 | B2 | 9/2006 | German |
| 7,132,662 | B2* | 11/2006 | Baldwin et al. ........... 250/361 R |
| 7,219,024 | B2 | 5/2007 | Gamache et al. |
| 7,373,504 | B1 | 5/2008 | Belgaied et al. |
| 7,376,530 | B2 | 5/2008 | Bienvenu et al. |
| 7,569,810 | B1 | 8/2009 | Troxler et al. |
| 7,581,446 | B2 | 9/2009 | Troxler |
| 7,605,366 | B2 | 10/2009 | Dep et al. |
| 7,705,614 | B2 | 4/2010 | Troxler et al. |
| 7,820,960 | B2 | 10/2010 | Troxler |
| 7,872,222 | B1 | 1/2011 | Dep et al. |
| 7,928,360 | B2 | 4/2011 | Troxler |
| 8,011,248 | B2 | 9/2011 | Troxler |
| 8,071,937 | B2 | 12/2011 | Troxler |
| 8,164,048 | B2 | 4/2012 | Weger et al. |
| 8,410,423 | B2 | 4/2013 | Bartlett et al. |
| 2001/0055363 | A1* | 12/2001 | Troxler et al. ................. 378/55 |
| 2002/0149617 | A1 | 10/2002 | Becker |
| 2003/0038634 | A1 | 2/2003 | Strack |
| 2003/0141464 | A1* | 7/2003 | Weger et al. ............... 250/498.1 |
| 2003/0222662 | A1 | 12/2003 | Geisel |
| 2004/0073382 | A1 | 4/2004 | Troxler et al. |
| 2004/0095154 | A1 | 5/2004 | Lundstrom et al. |
| 2004/0260504 | A1 | 12/2004 | Bienvenu et al. |
| 2005/0150278 | A1 | 7/2005 | Troxler et al. |
| 2005/0253703 | A1* | 11/2005 | He et al. ................... 340/539.13 |
| 2005/0267700 | A1 | 12/2005 | Gamache et al. |
| 2006/0273211 | A1 | 12/2006 | Langberg et al. |
| 2007/0216573 | A1 | 9/2007 | Handermann et al. |
| 2009/0194676 | A1 | 8/2009 | Weger et al. |
| 2009/0250599 | A1 | 10/2009 | Bartlett et al. |
| 2009/0314090 | A1 | 12/2009 | Troxler |
| 2011/0035182 | A1 | 2/2011 | Troxler |
| 2011/0194672 | A1 | 8/2011 | Troxler |
| 2012/0056627 | A1 | 3/2012 | Troxler |
| 2012/0169456 | A1 | 7/2012 | Weger et al. |

FOREIGN PATENT DOCUMENTS

| | | |
|---|---|---|
| EP | 1 943 479 | 7/2008 |
| GB | 863886 | 3/1961 |
| GB | 1284295 | 8/1972 |
| WO | WO 02/03055 | 1/2002 |
| WO | WO 2007/027760 | 3/2007 |
| WO | WO 2007/027797 | 3/2007 |
| WO | WO 2009/089172 A2 | 7/2009 |

OTHER PUBLICATIONS

Interview Summary for U.S. Appl. No. 12/348,841 (May 17, 2012).

Commonly-assigned, co-pending U.S. Appl. No. 13/414,680 for "Nuclear Gauges and Methods of Configuration and Calibration of Nuclear Gauges,"(Unpublished, filed Mar. 7, 2012).

Non-Final Official Action for U.S. Appl. No. 12/348,841 (Feb. 28, 2012).

First Office Action for Chinese Patent Application No. 200980107515.9 (Jan. 11, 2012).

Notice of Allowance and Fee(s) Due for U.S. Appl. No. 12/348,821 (Dec. 23, 2011).

Restriction Requirement for U.S. Appl. No. 12/348,841 (Nov. 7, 2011).

Restriction Requirement for U.S. Appl. No. 12/348,821 (Sep. 6, 2011).

Commonly-assigned, co-pending U.S. Appl. No. 13/225,386 for "Methods, Systems, and Computer Program Products for Determining a Property of Construction Material," (Unpublished, filed Sep. 2, 2011).

Restriction Requirement for U.S. Appl. No. 12/348,841 (Aug. 22, 2011).

First Office Action for Chinese Patent Application No. 200680040289.3 (Jul. 19, 2011).

Notification of Transmittal of International Preliminary Report on Patentability for International Application No. PCT/US06/33839 (Jul. 13, 2011).

Notice of Allowance and Fee(s) Due for U.S. Appl. No. 13/089,196 (Jun. 28, 2011).

Notice of Granting Patent Right for Invention for Chinese Patent Application No. 200680040215.X (May 25, 2011).

Notice of Allowance and Fee(s) Due for U.S. Appl. No. 12/551,241 (May 11, 2011).

Commonly-assigned, co-pending U.S. Appl. No. 13/089,196 for "Methods, Systems, and Computer Program Products for Measuring the Density of Material Including a Non-Nuclear Moisture Property Detector," (Unpublished, filed Apr. 18, 2011).

Supplementary European Search Report for European Patent No. 1932020 (Jan. 20, 2011).

Notice of Allowance and Fee(s) Due for U.S. Appl. No. 12/910,745 (Dec. 13, 2010).

Communication of European publication number and information on the application of Article 67(3) EPC for International Application No. PCT/US09/30136 (Sep. 15, 2010).

Non-Final Official Action for U.S. Appl. No. 12/551,241 (Sep. 8, 2010).

Notification of Transmittal of the International Preliminary Report on Patentability for International Application No. PCT/US09/30136 (Jul. 15, 2010).

Notice of Allowance and Fee(s) Due for U.S. Appl. No. 12/534,739 (Jun. 17, 2010).

Official Action for Chinese Patent Application No. 200680040215.X (Apr. 29, 2010).

Official Action for Chinese Patent Application No. 200680040215.X (Dec. 18, 2009).

Notification of Transmittal of the International Search Report and the Written Opinion of the International Searching Authority, or the Declaration for International Application No. PCT/US09/30136 (Jul. 15, 2009).

Notice of Allowance and Issue Fee(s) Due for U.S. Appl. No. 11/513,334 (Jun. 12, 2009).

Notice of Allowance and Issue Fee(s) Due for U.S. Appl. No. 11/512,732 (May 29, 2009).

Final Official Action for U.S. Appl. No. 11/513,334 (Oct. 30, 2008).

Official Action for U.S. Appl. No. 11/512,732 (Sep. 11, 2008).

Notification of Transmittal of International Preliminary Report on Patentability for International Application No.PCT/US2006/033898 (Jun. 23, 2008).

(56) References Cited

OTHER PUBLICATIONS

Notification of Transmittal of the International Search Report and The Written Opinion of the International Searching Authority, or the Declaration for International Application No. PCT/US2006/033839 (May 29, 2008).

Notification Concerning Trasmittal of International Preliminary Report on Patentability for International Application No. PCT/US2006/033898 (Mar. 13, 2008).

Official Action for U.S. Appl. No. 11/513,334 (Jan. 29, 2008).

Notification of Transmittal of the International Search Report and the Written Opinion of the International Searching Authority, or the Declaration of International Application No. PCT/US2006/033898 (Sep. 26, 2007).

Restriction Requirement for U.S. Appl. No. 11/513,334 (Sep. 13, 2007).

Troxler Electronic Laboratories "Model 6180 Troxler Tracker™ Calibration Tracking System, Manual of Operation and Instruction," PN109315, Edition 2.0 pp. 1-94 (Aug. 2007).

Sebesta et al., "New Technologies and Approaches to Controlling the Quality of Flexible Pavement Construction Performed in Cooperation with the Texas Department of Transportation and the Federal Highway Administration," Texas Transportation Institute, Report 0-4774-1 (Jun. 2006).

U.S. Department of the Army, "Engineering and Design Site Characterization and Analysis Penetrometer System (SCAPS)," EP 1110-1-32, pp. 1-14 (Nov. 1, 2005).

Kim et al., "Typical Dynamic Moduli for North Carolina Asphalt Concrete Mixtures," Final Report FWHA/NC, 2005-03 (May 2005).

Balendonck et al., "Sensors for Soil, Substrates, and Concrete Based on the MCM100 Microchip," Electromagnetic Aquametry, Springer (2005).

Chen et al., "A Correlation Between Dynamic Cone Penetrometer Values and Pavement Layer Moduli," Geotechnical Testing Journal, vol. 28, No. 1 (2005).

Daschner et al., "Determination of Composition of Foodstuffs Using MW Dielectric Spectra," Electromagnetic Aquametry, Springer, pp. 455-461 (2005).

Hauschild, "Density and Moisture Measurements Using Microwave Resonators," Electromagnetic Aquametry, Springer (2005).

Huebner et al., "Advanced Measurement Methods in Time Domain Reflectometry for Soil Moisture Determination," Electromagnetic Aquametry, Springer (2005).

Jones et al., "Thermal and Geometrical Effects on Bulk Permittivity of Porous Mixtures Containing Bound Water," Electromagnetic Aquametry, Springer (2005).

Kaatze, "Electromagnetic Wave Interactions with Water and Aqueous Solutions," Electromagnetic Aquametry, Springer (2005).

Kraszewski, "Recent Developments in Electromagnetic Aquametry," Electromagnetic Aquametry, Springer, pp. 6-11 (2005).

Kupfer, "Methods of Density-Independent Moisture Measurement," Electromagnetic Aquametry, Springer, pp. 135-165 (2005).

Kupfer, "Simulations and Experiments for Detection of Moisture Profiles with TDR in a Saline Environment," Electromagnetic Aquametry, Springer, pp. 349-365 (2005).

Sachs, "Principles of Ultra-Wideband Sensor Electronics," Electromagnetic Aquametry, Springer (2005).

Sihvola, "Model Systems for Materials with High Dielectric Losses in Aquametry," Electromagnetic Aquametry, Springer (2005).

Sovlukov, "Microwave and RF Resonator-Based Aquametry," Electromagnetic Aquametry, Springer (2005).

Stacheder et al. "Combined TDR and Low-Frequency Permittivity Measurements for Continuous Snow Wetness and Snow Density Determination," Electromagnetic Aquametry, Springer (2005).

Thakur, "Moisture Measurement in Multi-Layered Systems," Electromagnetic Aquametry, Springer (2005).

Wolter et al., "Moisture Measuring with Nuclear Magnetic Resonance (NMR)," Electromagnetic Aquametry, Springer (2005).

Zeghal et al., "Review of the New Mechanistic-Empirical Pavement Design Guide—A Material Characterization Perspective," Investing in New Materials, Products and Processes Session—2005 Annual Conference, Transportation Association of Canada, Calgery, Alberta (2005).

Hoffmann et al., "Stiffness Estimates Using Portable Deflectometers," TRB Annual Meeting (2004), Washington, D.C. (2004).

Olidis et al., "Guide for the Mechanistic-Empirical Design of New and Rehabilitated Pavement Structures Materials Characterization—Is Your Agency Ready?" Applied Research Associates, Inc.—ERES Consultants Division (2004).

Sun et al., "Evaluation of a Combined Penetrometer for Simultaneous Measurement of Penetration Resistance and Soil Water Content," Journal of Plant Nutr. Soil Science, vol. 167, pp. 745-751 (2004).

Nazarian et al., "Quality Management of Flexible Pavement Layers with Seismic Methods," Center for Highway Materials Research, Research Report 1735-3F, pp. 1-40 (Dec. 2002) (Part 1 of 3).

Nazarian et al., "Quality Management of Flexible Pavement Layers with Seismic Methods," Center for Highway Materials Research, Research Report 1735-3F, pp. 41-80 (Dec. 2002) (Part 2 of 3).

Nazarian et al., "Quality Management of Flexible Pavement Layers with Seismic Methods," Center for Highway Materials Research, Research Report 1735-3F, pp. 81-120 (Dec. 2002) (Part 3 of 3).

Nelson et al, "RF Sensing of Grain and Seed Moisture Content," IEEE Sensors Journal, vol. 1, No. 2, pp. 119-126 (Aug. 2001).

Vaz et al., "Simultaneous Measurement of Soil Penetration Resistance and Water Content with a Combined Penetrometer-TDR Moisture Probe," Soil Soc. Am. Journal, vol. 65, pp. 4-12 (2001).

Nazarian et al., "Compaction Quality Control of Soils Using Wave Propagation Techniques," Center for Highway Materials Research, The University of Texas at El Paso, TRB 2001 Washington D.C. (Nov. 2000).

Newtson et al., "Nondestructive Evaluation Using Numerical Simulation of Impact Response," ACI Materials Journal (May-Jun. 2000).

Gucunski et al., "Seismic Methods in Post Construction Condition Monitoring of Bridge Decks," Use of Geophysical Methods in Construction, Proceedings Geo-Denver (2000).

Gucunski et al., "Ann Backcalculation of Pavement Profiles from the SASW Test," Pavement Subgrade Unbound Materials and NonDestructive Testing, ED. M. Mamlouk, ASCE, Geo-Denver (2000).

Russell et al., "Design of Resilient Modulus of Subgrade Soils from FWD Tests," Pavement Subgrade Unbound Materials and NonDestructive Testing, ED. M. Mamlouk, ASCE, Geo-Denver (2000).

Nazarian et al., "Use of Instrumented Dynamic Cone Penetrometer in Pavement Characterization," Third International Symposium on Nondestructive Testing of Pavements and Backcalculation of Moduli, ASTM Stock No. STP1375, pp. 214-228 (Jul. 1, 1999).

Chen et al., "Evaluation of In-Situ Resilient Modulus Testing Techniques," Recent Advances in the Characterization of Transportation Geo-Materials, ASCE, No. 89 (1999).

Newcomb et al., "Measuring In Situ Mechanical Properties of Pavement Subgrade Soils," Synthesis of Highway Practice 278, NCHRP, Washington DC (1999).

"C-300 Operator's Manual," Seaman Nuclear Corporation, pp. 1-80 (Copyright 1999).

Sabburg et al., "Dielectric Behavior of Moist Swelling Clay Soils at Microwave Frequencies," IEEE Transactions on Geoscience and Remote Sensing, vol. 35, No. 3, pp. 784-787 (May 1997).

Lunne et al., "Cone Penetration Testing in Geotechnical Practice," Blackie Academic and Professional Publishing (1997).

Trabelsi et al., "New Density-Independent Calibration Function for Microwave Sensing of Moisture Content in Particulate Materials," IEEE Transactions on Instrumentation and Measurement, vol. 47, No. 3, pp. 613-622 (Jun. 1998).

Trabelsi et al., "A Microwave Method for On-Line Determination of Bulk Density and Moisture Content of Particulate Materials," IEEE Transactions on Instrumentation and Measurement, vol. 47, No. 1, pp. 127-132 (Feb. 1998).

Cutmore et al., "On-Line Measurement of Composition for the Australian Mineral and Energy Industries," IEEE Instrumentation and Measurement Technology Conference, Belgium, pp. 330-334 (Jun. 4-6, 1996).

(56) References Cited

OTHER PUBLICATIONS

Peplinski et al., "Dielectric Properties of Soils in the 0.3-1.3-GHz Range," IEEE Transactions on Geoscience and Remote Sensing, vol. 33, No. 3 (May 1995).
Vermeulen et al., "Continuous Measurement of Moisture in Nonconducting Materials," IEEE Transactions on Instrumentation and Measurement, vol. 41, No. 6, pp. 1023-1026 (Dec. 1992).
Scott et al., "Measured Electrical Constitutive Parameters of Soil as Functions of Frequencey and Moisture Content," IEEE Transactions on Geoscience and Remote Sensing, vol. 30, No. 3, pp. 621-623 (May 1992).
Thuery, "Microwaves: Industrial Scientific and Medical Applications," Artec House, (1992).
Kraszewski, "Microwave Aquametry—Needs and Perspectives," IEE MTT, vol. 39, No. 5, pp. 828-835 (May 1991).
Arulanandan, "Dielectric Method for Prediction of Porosity of Saturated Soil," Journal of Geotechnical Engineering, vol. 117, No. 2, pp. 319-330 (Feb. 1991).
Roesset et al., "Modulus and Thickness of the Pavement Surface Layer from SASW Tests," Transportation Research Record 1260 (1990).
Badu-Tweneboah et al., "Prediction of Flexible Pavement Layer Moduli from Dynaflect and FWD Deflections," Nondestructive Testing of Pavements and Backcalculation of Moduli, ASTM STP 1026 (1989).
Chou et al., "Backcalculation of Layer Moduli from Nondestructive Pavement Deflection Data Using the Expert System Approach," Nondestructive Testing of Pavements and Backcalculation of Moduli, ASTM STP 1026 (1989).
Cosentino et al., "FWD Backcalculated Moduli Compared with Pavement Pressuremeter Moduli and Cyclic Triaxial Moduli," Nondestructive Testing of Pavements and Backcalculation of Moduli, ASTM STP 1026 (1989).
Germann et al., "Temperature, Frequency, and Load Level Correction Factors for Backcalculated Moduli Values," Nondestructive Testing of Pavements and Backcalculation of Moduli, ASTM STP 1026 (1989).
Hiltunen et al., "Influence of Source and Receiver Geometry on the Testing of Pavements by the Surface Waves Method," Nondestructive Testing of Pavements and Backcalculation of Moduli, ASTM STP 1026 (1989).
Hossain et al., "Numerical and Optimization Techniques Applied to Surface Waves for Backcalculation of Layer Moduli," Nondestructive Testing of Pavements and Backcalculation of Moduli, ASTM STP 1026 (1989).
Lytton, "Backcalculation of Pavement Layer Properties," Nondestructive Testing of Pavements and Backcalculation of Moduli, ASTM STP 1026 (1989).
Nazarian et al., "Nondestructive Evaluation of Pavements by Surface Wave Method," Nondestructive Testing of Pavements and Backcalculation of Moduli, ASTM STP 1026 (1989).
Sayyedsadr et al., "SASWOPR: A Program to Operated on Spectral Analysis of Surface Wave Data," Nondestructive Testing of Pavements and Backcalculation of Moduli, ASTM STP 1026 (1989).
Uddin et al., "In Situ Material Properties from Dynamic Deflection Equipment," Nondestructive Testing of Pavements and Backcalculation of Moduli, ASTM STP 1026 (1989).
Powell et al., "Use of a Density-Independent Function and Microwave Measurement System for Grain Moisture and Measurement," Transactions of ASAE, vol. 31, No. 6 (Nov.-Dec. 1988).
Dean et al., "Soil Moisture Measurement by an Improved Capacitance Technique, Part 1, Sensor Design and Performance," Journal of Hydrology, vol. 93, pp. 67-78 (1987).
Shimin, "A New Method for Measuring Dielectric Constant Using the Resonant Ferquency of a Patch Antenna," IEEE MTT—34, No. 9, pp. 923-931 (Sep. 1986).
Lew et al., "Relationships Between Shear Wave Velocity and Depth of Overburden," Measurement and Use of Shear Wave Velocity for Evaluating Dynamic Soil Properties, ASCE (1985).

Robertson et al., "Seismic CPT to Measure In-Situ Shear Wave Velocity," Measurement and Use of Shear Wave Velocity for Evaluating Dynamic Soil Properties, ASCE (1985).
Stokoe et al., "Use of Rayleigh Waves in Liquefaction Studies," Measurement and Use of Shear Wave Velocity for Evaluating Dynamic Soil Properties, ASCE (1985).
Stoll, "Computer-Aided Studies of Complex Soil Moduli," Measurement and Use of Shear Wave Velocity for Evaluating Dynamic Soil Properties, ASCE (1985).
Heisey et al., "Moduli of Pavement Systems from Spectral Analysis of Surface Waves", Transportation Research Record 852 (1983).
Kuraz, "Testing of a Field Dielectric Soil Moisture Meter," Geotechnical Testing Journal, vol. 4, No. 3, pp. 111-116 (Sep. 1981).
Meyer et al., "Feasibility Study of Density-Independent Moisture Measurement with Microwaves," IEEE MTT—29, pp. 732-739 (Jul. 1981).
Holtz "Introduction to Geotechnical Engineering" Prentice Hall (1981).
Topp, "Electromagnetic Determination of Soil Water Content: Measurements in Coaxial Transmission Lines," Water Resources Research, vol. 16, No. 3, pp. 574-582 (Jun. 1980).
Wobschall, "A Frequency Shift Dielectric Soil Moisture Sensor," IEEE Transaction of Geoscience Electronics, vol. GE-16, No. 2 (Apr. 1978).
Kraszewski et al., "A Preliminary Study Microwave Monitoring of Moisture Content in Wheat," Journal of Microwave Power, vol. 12, No. 3, pp. 241-255 (Sep. 1977).
Drnevich et al., "Modulus and Damping of Soils by the Resonant Column Method," Dynamic Geotechnical Testing, ASTM STP 654, Denver, CO (Jun. 1977).
Hoar et al., "Generation and Measurement of Shear Waves In Situ," Dynamic Geotechnical Testing, ASTM STP 654, Denver, CO (Jun. 1977).
McLamore et al., "Crosshole Testing Using Explosive and Mechanical Energy Sources," Dynamic Geotechnical Testing, ASTM STP 654, pp. 30-55 (Jun. 1977).
Statton et al., "In Situ Seismic Shear-Wave Velocity Measurements and Proposed Procedures," Dynamic Geotechnical Testing, ASTM STP 654, Denver, CO (Jun. 1977).
Stephenson, "Ultrasonic Testing for Determining Dynamic Soil Moduli," Dynamic Geotechnical Testing, ASTM STP 654, Denver, CO (Jun. 1977).
Wobschall, "A Theory of the Complex Dielectric Permittivity of Soil Containing Water," IEEE Transaction on Geoscience Electron, vol. GE-15, No. 1, pp. 49-58 (1977).
Anderson et al., "Comparison of Field and Laboratory Shear Moduli," In Situ Measurement of Soil Properties, vol. I, North Carolina State University, Raleigh, NC, ASCE (Jun. 1-4, 1975).
Miller et al., "In Situ Impulse Test for Dynamic Shear Modulus of Soils." In Situ Measurement of Soil Properties, vol. I, North Carolina State University, Raleigh, NC, ASCE 1975 (Jun. 1-4, 1975).
Stokoe et al., "Shear Moduli of Two Compacted Fills," In Situ Measurement of Soil Properties, vol. I, North Carolina State University, Raleigh, NC, ASCE (Jun. 1-4, 1975).
Windle et al., "Electrical Resistivity Method for Determining Volume Changes that Occur During a Pressuremeter Test," In Situ Measurement of Soil Properties, vol. I, North Carolina State University, Raleigh, NC, ASCE 1975 (Jun. 1-4, 1975).
Wissa et al., "The Piezometer Probe," In Situ Measurement of Soil Properties, vol. I, North Carolina State University, Raleigh, NC, ASCE 1975 (Jun. 1-4, 1975).
Birchak et al., "High Dielectric Constant Microwave Probes for Sensing Soil Moisture," Proceedings of the IEEE, vol. 62, No. 1, pp. 93-98 (Jan. 1974).
Hipp, "Soil Electromagnetic Parameters as Functions of Frequency, Soil Density and Soil Moisture," Proceedings of the IEEE, vol. 62, No. 1, pp. 98-103 (Jan. 1974).
Hoekstra et al., "Dielectric Properties of Soils at UHF and Microwave Frequencies," Journal of Geophysical Research, vol. 79, pp. 1699-1708 (1974).
Henkel, "The Relationships Between the Effective Stresses and Water Content in Saturated Clays," Geotechnique, vol. 10 (1960).

(56) References Cited

OTHER PUBLICATIONS

Henkel, "The Shear Strength of Saturated Remolded Clays," Proceedings of Research Conference on Shear Strength of Cohesive Soils, ASCE, pp. 533-554 (1960).

Benson, "An Overview of Geophysical and Non-Destructive Methods for Characterization of Roads and Bridges," Use of Geophysical Methods in Construction, ASCE, 108 (2000).

Bose et al., "Dielectric Relaxation Study of Water and Water/Oil Microemulsion System," Microwave Aquametry—Electromagnetic Wave Interaction with Water-Containing Materials, IEEE (Apr. 1996).

Brandelik et al., "Measurement of Bound and Free Water in Mixtures," Microwave Aquametry—Electromagnetic Wave Interaction with Water-Containing Materials, IEEE (1996).

Gentili et al., "Analysis of Electromagnetic Sensors for Dielectric Spectroscopy by Using the (FD)2TD Method," Microwave Aquametry—Electromagnetic Wave Interaction with Water-Containing Materials, IEEE (Apr. 1996).

Gentili et al., "An Integrated Microwave Moisture Sensor," Microwave Aquametry—Electromagnetic Wave Interaction with Water-Containing Materials, IEEE (1996).

Griffin et al., "Precision of Seismic Wave Propagation Methods in Construction Applications," Use of Geophysical Methods in Construction, ASCE, 108 (2000).

Guzina, "Dynamic Soil Sensing via Horizontally-Polarized Shear Waves," Use of Geophysical Methods in Construction, ASCE, 108 (2000).

Guzina et al., "Verification and Enhancement of Portable Deflectometer Devices," http://www.mrr.dot.state.mn.us/research/MnROAD_Project/workshop2003/Base_Subgrade_Characterization_Devices.pdf (2003).

Jung, "Application of Electrical Resistivity Imaging Techniques to Civil & Environmental Problems," Use of Geophysical Methods in Construction, ASCE, 108 (2000).

Kaatze "Microwave Dielectric Properties of Water," Microwave Aquametry—Electromagnetic Wave Interaction with Water-Containing Materials, IEEE (1996).

Kendra et al., "Snow Probe for in Situ Determination of Wetness and Density," Microwave Aquametry—Electromagnetic Wave Interaction with Water-Containing Materials, IEEE (Aug. 2002).

King et al., "Material Characterization Using Microwave Open Reflection Resonator Sensors," Microwave Aquametry—Electromagnetic Wave Interaction with Water-Containing Materials, IEEE (1994).

Kobayashi, "Microwave Attenuation in a Wet Layer of Limestone," Microwave Aquametry—Electromagnetic Wave Interaction with Water-Containing Materials, IEEE (1996).

Kraszewski, "Microwave Aquametry: Introduction to the Workshop," Microwave Aquametry—Electromagnetic Wave Interaction with Water-Containing Materials, IEEE (1996).

Kraszewski et al., "Moisture Content Determination in Single Kernels and Seeds with Microwave Resonant Sensors," Microwave Aquametry—Electromagnetic Wave Interaction with Water-Containing Materials, IEEE (1996).

Kupfer, "Possibilities and Limitations of Density-Independent Moisture Measurement with Microwaves," Microwave Aquametry—Electromagnetic Wave Interaction with Water-Containing Materials, IEEE, pp. 313-327 (1996).

Lin et al., "Time Domain Reflectometry for Compaction Quality Control," Use of Geophysical Methods in Construction, ASCE, 108 (2000).

Mashimo, "Free and Bound Water in Various Matrix Systems Studied by Advanced Microwave Techniques," Microwave Aquametry—Electromagnetic Wave Interaction with Water-Containing Materials, IEEE, pp. 93-99 (1997).

Robinson et al., "Single- and Multiple-Frequency Phase Change Methods for Microwave Moisture Measurement," Microwave Aquametry—Electromagnetic Wave Interaction with Water-Containing Materials, IEEE (1996).

Sihvola, "Dielectric Mixture Theories in Permittivity prediction: Effects of Water on Macroscopic Parameters," Microwave Aquametry—Electromagnetic Wave Interaction with Water-Containing Materials, IEEE (1996).

Volgyi, "Integrated Microwave Moisture Sensors for Automatic Process Control," Microwave Aquametry—Electromagnetic Wave Interaction with Water-Containing Materials, IEEE, pp. 223-238 (1996).

Walker, "Accurate Percent Water Determination by Microwave Interaction Alone: 1954-Present," Microwave Aquametry—Electromagnetic Wave Interaction with Water-Containing Materials, IEEE (Apr. 1996).

Wang et al., "SH-Wave Refraction/Reflection and Site Characterization," Use of Geophysical Methods in Construction, ASCE, 108 (2000).

Xu et al., "Calculation of Sensitivity of Various Coaxial Sensors Used in Microwave Permittivity Measurements," Microwave Aquametry—Electromagnetic Wave Interaction with Water-Containing Materials, IEEE (Apr. 1996).

Notice of Allowance and Fee(s) Due for U.S. Appl. No. 12/348,841 (Dec. 12, 2012).

Final Official Action for U.S. Appl. No. 12/348,841 (Nov. 21, 2012).

Second Office Action for Chinese Patent Application No. 200980107515.9 (Oct. 18, 2012).

Non-Final Official Action for U.S. Appl. No. 12/348,841 (Jun. 14, 2012).

Second Office Action for Chinese Patent Application No. 200680040289.3 (Jun. 6, 2012).

Third Office Action for Chinese Patent Application No. 200680040289.3 (Feb. 26, 2013).

Final Official Action for U.S. Appl. No. 13/414,680 (Feb. 8, 2013).

\* cited by examiner

FIG. 18B  FIG. 18C

NUCLEAR GAUGES AND RELATED METHODS OF ASSEMBLY

RELATED APPLICATIONS

The presently disclosed subject matter claims the benefit of U.S. Provisional Patent Application Ser. Nos. 61/010,103, 61/010,022, and 61/010,191, all filed Jan. 4, 2008; the disclosures of which are incorporated herein by reference in their entirety.

TECHNICAL FIELD

The present subject matter generally relates to an apparatus and method for determining the density and/or moisture of materials and, more particularly, relates to nuclear gauges used in measuring the density and/or moisture of construction-related materials.

BACKGROUND

Nuclear radiation gauges have been widely used for measuring the density and moisture of soil and asphaltic materials, or other construction material. As used herein, construction material is any materials used in building roads or foundational structures including, but not limited to soils, asphalts, asphalt-like materials, concrete, composite materials, or the like. Such gauges typically include a source of gamma radiation which directs gamma radiation into the test material, and a radiation detector located adjacent to the surface of the test material for detecting radiation scattered back to the surface. From this detector reading, a determination of the moisture and density of the material can be made.

These gauges are generally designed to operate either in a "backscatter" mode or in both a backscatter mode and direct transmission mode. In gauges capable of direct transmission mode, the radiation source is vertically moveable from a backscatter position, where it resides within the gauge housing, to a series of direct transmission positions, where it is inserted into small holes or bores in the test specimen.

Many of the gauges commonly in use for measuring density of soil, asphalt and other materials are most effective in measuring densities of materials over depths of approximately 3 to 12 inches. However, with the increase in cost of paving materials, the practice in maintaining and resurfacing paved roadbeds has become one of applying relatively thin layers or overlays having a thickness of one to three inches. With layers of such a thickness range, many density gauges are ineffective for measuring the density of the overlay because the density reading obtained from such gauges reflects not only the density of the thin layer, but also the density of the underlying base material.

Nuclear gauges capable of measuring the density of thin layers of materials have been developed by Troxler Electronic Laboratories, Inc. of Research Triangle Park, N.C. For example, thin layer density gauges are disclosed in U.S. Pat. Nos. 4,525,854, 4,701,868, 4,641,030, 6,310,936 and 6,442,232, all of which are incorporated herein by reference in their entirety. Some of the gauges disclosed in the above-referenced patents are referred to as "backscatter" gauges because the radiation source does not move outside the gauge housing, which is necessary for measurement in the direct transmission mode. In some of the gauges disclosed in the above-referenced patents, the gauge can have radiation sources that can also be extended outside of the gauge housing and into the material to be measured in a direction transmission mode. Typically, the source rods can extend up to about 12 inches.

As disclosed in the above patents, the preferred method of measuring the density of thin layers of materials, such as asphalt, is nondestructive and uses the backscatter mode. One method requires two independent density measurement systems. The geometry of these two measurement systems must be configured with respect to one another and with respect to the medium being measured in such a manner that they measure two different volumes of material. The two different volumes are not mutually exclusive insofar as they partially overlap one another. Measurement accuracy depends upon a larger portion of the volume measured by one of the measurement systems being distributed at a lower depth beneath the gauge than the volume measured by the other measurement system. This is accomplished by placing one radiation detection system in closer spatial proximity to the radiation source than the other detection system. Another volume specific measurement is typically used in soils and requires drilling a small hole in the material under test. This method is referred to as the direct transmission mode.

To provide proper position of the movable radiation source in some nuclear gauges, index positions were cut mechanically into the source rod. This source rod is problematic to precisely set and adjust and adds to the overall product cost. In other nuclear gauges, the means for extending and retracting included an index rod operatively positioned adjacent to the source rod. The index rod included a plurality of notches. Each notch corresponds to a predetermined source rod position. For example, one notch corresponds to the "safe" position wherein the radiation source was raised and shielded from the test material. Other notches can correspond to positions that place the source up to about 12 inches in the material. These indexing rods have been also been problematic to set and also add to the overall product cost.

There remains a need in the art for a nuclear gauge capable of operating in backscatter mode and/or direct transmission mode, and which is suitable for measuring the density and moisture of construction material.

SUMMARY

In accordance with this disclosure, nuclear gauges for determining the density and/or moisture of materials, components of such nuclear gauges, and components and methods for assembly of the same are provided. It is, therefore, an object of the present disclosure to provide nuclear gauges used in measuring the density and/or moisture of construction-related materials and methods for assembly of the gauges and their components. This and other objects as may become apparent from the present disclosure are achieved, in whole or in part, by the subject matter described herein.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which:

FIGS. 18A-18C illustrate different views of an embodiment of a replaceable sliding guide for use in a nuclear gauge according to the present subject matter;

DETAILED DESCRIPTION

Reference will now be made in detail to the description of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

Nuclear Gauge Apparatus

Figure 1:
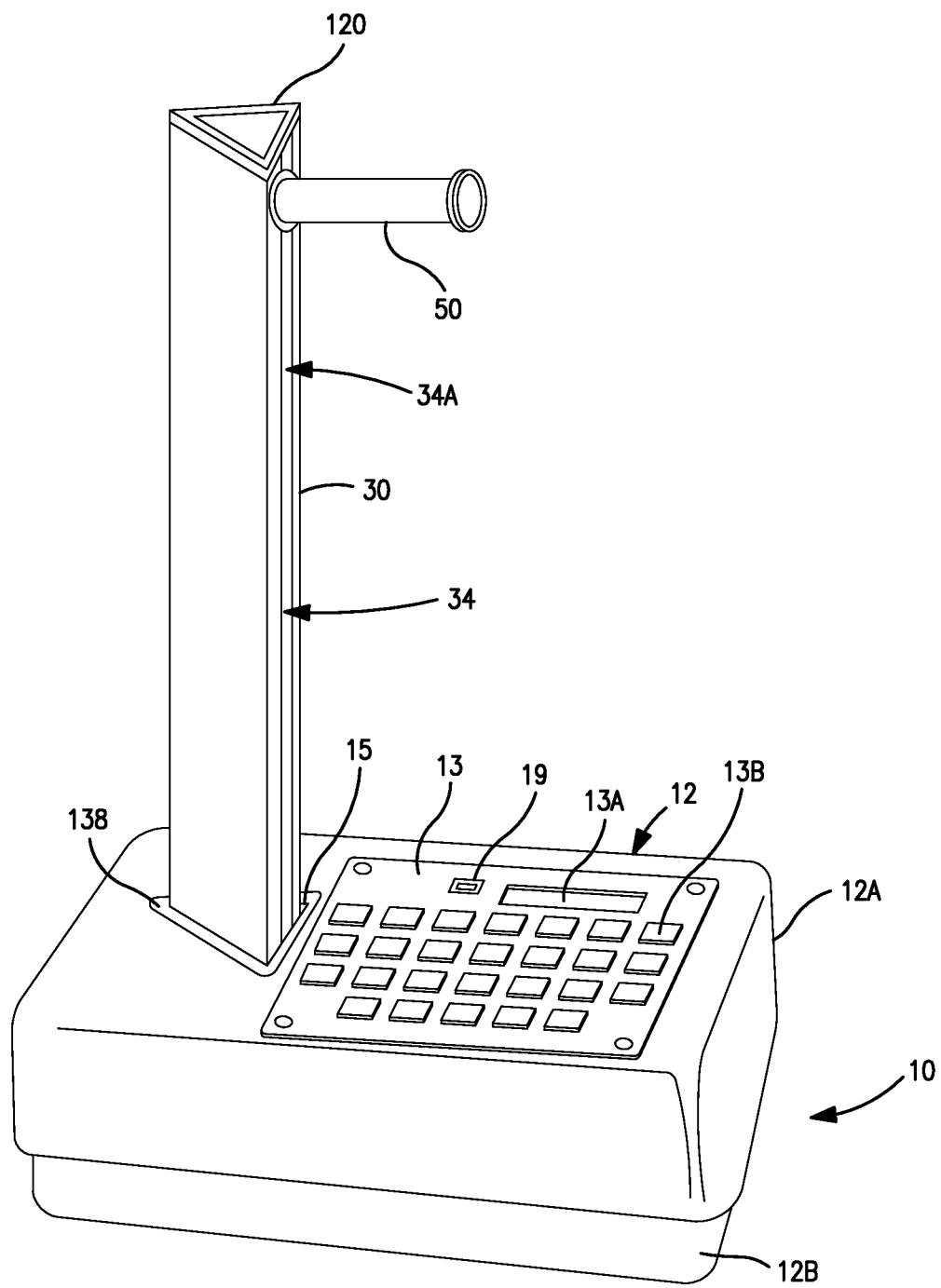
FIG. 1 illustrates a perspective view of an embodiment of a nuclear gauge according to the present subject matter.
Figure 2:
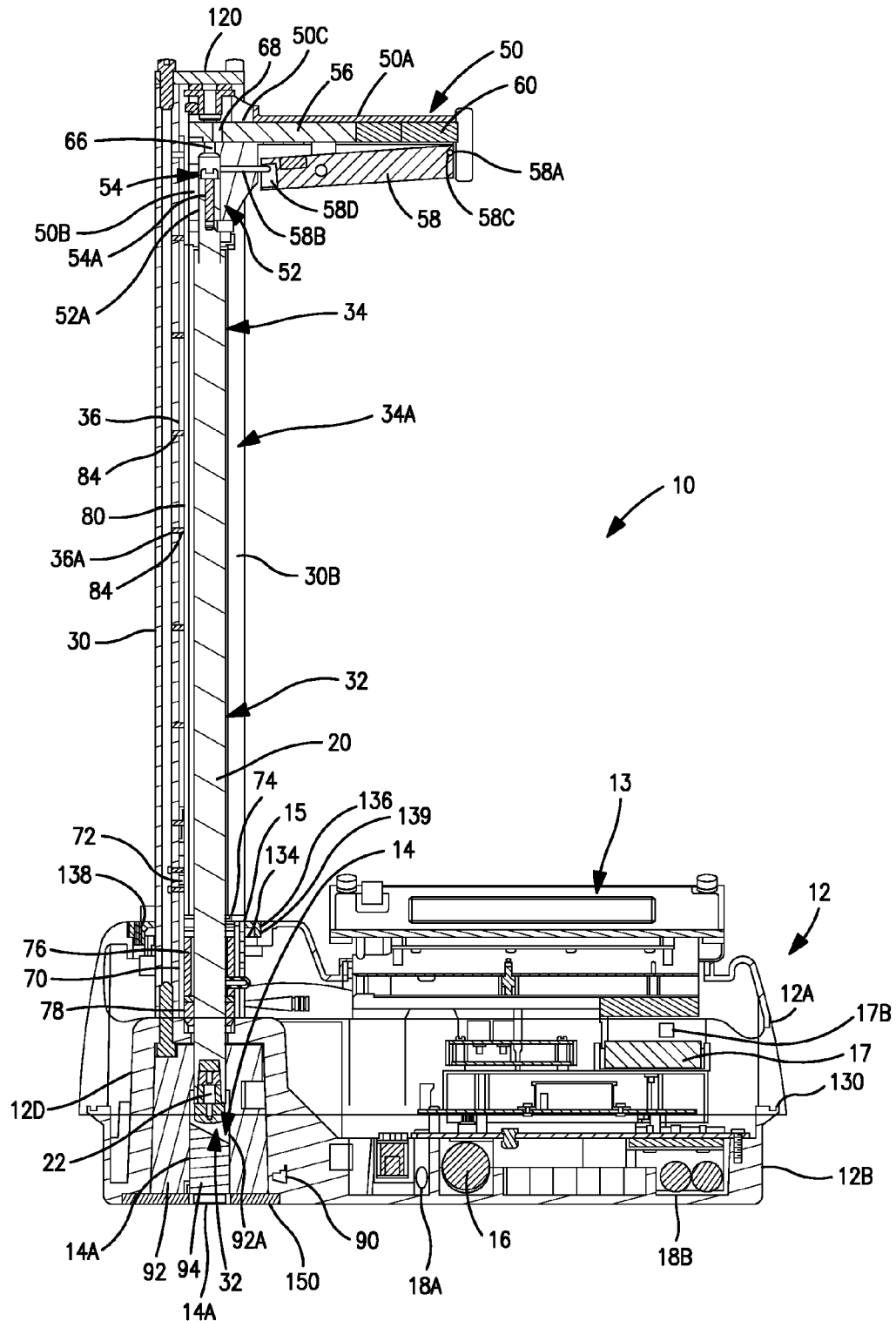
FIG. 2 illustrates a vertical cross-sectional view of the nuclear gauge illustrated in FIG. 1.
Figure 3:
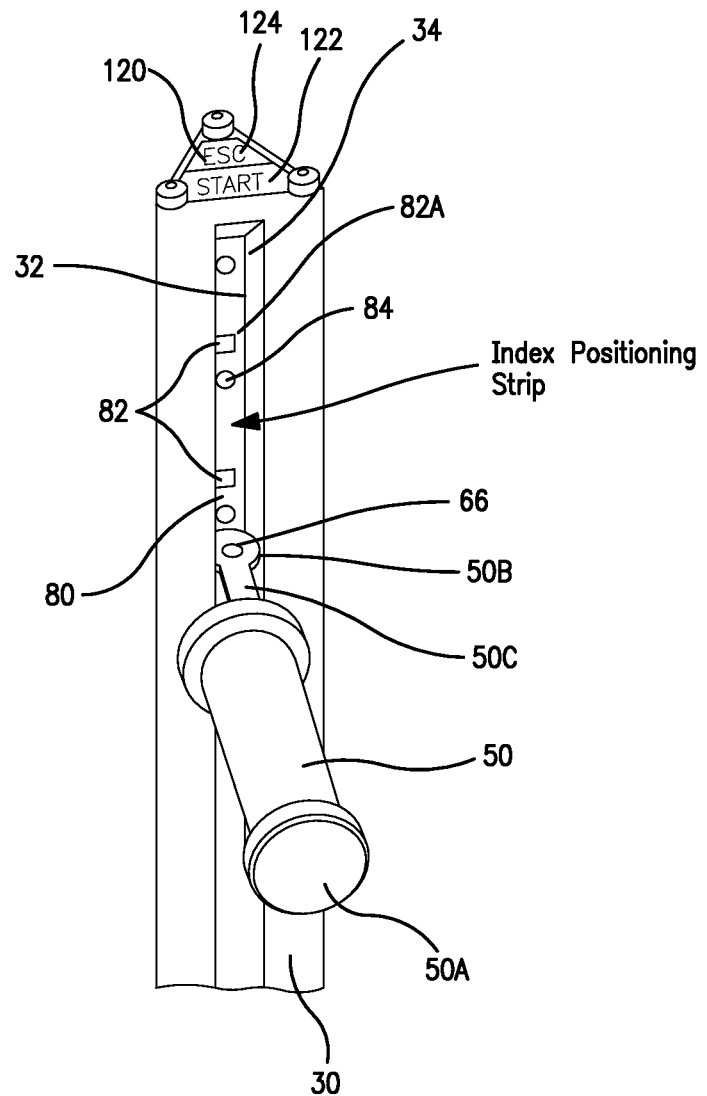
FIG. 3 illustrates a perspective view of a portion of the nuclear gauge illustrated in FIG. 1.

FIGS. 1 and 2 illustrate a nuclear gauge, generally designated 10. Different aspects and elements of gauge 10 will be briefly described with a more detailed description of the different elements provided further below. The nuclear gauge can be a density gauge, a bulk density gauge, a thin overlay gauge, and a thin layer gauge or combination thereof.

By way of example to explain the present subject matter, the gauge 10 depicted in the figures is a thin layer gauge. However, as stated above, the gauge 10 can be other configurations of nuclear gauges. The gauge 10 can be capable of accurately measuring the density of materials, for example, thin layers of materials such as asphalt, through the use of a scattered radiation that is detected by radiation detectors. The gauge 10 can operate in both backscatter and direct transmission modes. The gauge 10 can include a gauge housing 12 and a tower, or source rod housing, 30. The gauge housing 12 and the tower 30 can form a vertical conduit 32 that extends through both gauge housing 12 and tower 30. For example, the gauge housing 12 can have a vertical cavity 14 therein and the tower 30 can include a vertical channel 34 therein that can be aligned to create the vertical conduit 32. For instance, the gauge housing 12 can include a top cover 12A and a base 12B. The base 12B can include the vertical cavity 14 therethrough. The top can include an opening 15 through which the tower 30 can pass. The tower 30 can be disposed on the base 12B of the gauge housing 12 so that the vertical channel 32 aligns with the vertical cavity 14 to form a vertical conduit 34 through the tower 30 and the gauge housing 12.

The gauge 10 can include a user interface 13 that is located on the top cover 12A of the gauge housing 12. The user interface 13 can be in communication with a central processing unit (CPU) 17 that controls the gauge 10 and runs the associated tests. For example, the user interface 13 can include a screen 13A and keypad 13B that can be used to input the parameters of the tests to be run on the nuclear gauge 10.

Figure 14:
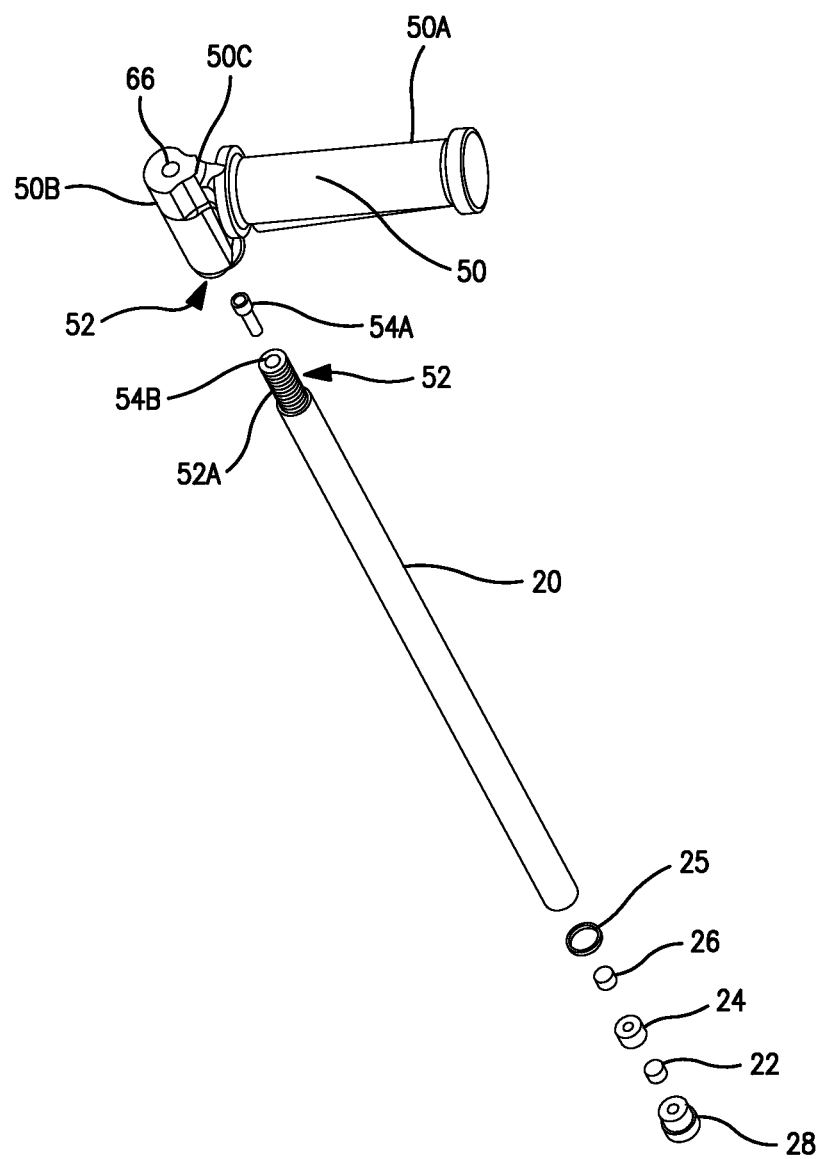
FIG. 14 illustrates an exploded view of an embodiment of a source rod and handle according to the present subject matter.
Figure 15:
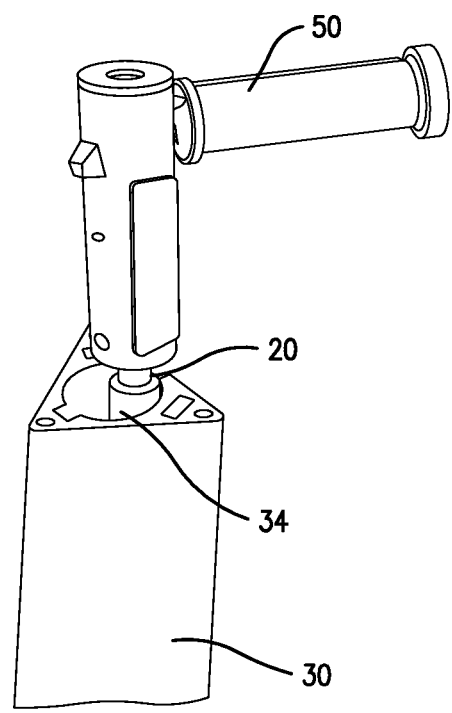
FIG. 15 illustrates a perspective view of an embodiment of a source rod being inserted a support tower, or source rod housing, according to the present subject matter.

The gauge 10 can include a vertically moveable source rod 20 containing a radiation source 22 in a distal end thereof. As shown in FIG. 14, the source rod 20 can include a spacer 24, a ring weld 25, a source spring 26 and a source plug 28. The radiation source 22 may be any suitable radiation source, such as $^{137}Cs$ radiation source or $^{60}Co$. The source rod 20 can reside in the vertical conduit 32 created by the vertical channel 34 of the tower 30 and the vertical cavity 14 in the gauge housing 12.

The gauge 10 can include at least one density measurement system that utilizes at least one radiation detector. For example, as shown in FIG. 2, the gauge 10 can include two separate density measurement systems. The geometry of these two measurement systems is configured with respect to one another and with respect to the medium being measured in such a manner that they measure two different volumes of material. The two different volumes are not mutually exclusive insofar as they partially overlap one another. Measurement accuracy depends upon a larger portion of the volume measured by one of the measurement systems being distributed at a lower depth beneath the gauge than the volume measured by the other measurement system. This is accomplished by placing one radiation detection system in closer spatial proximity to the radiation source than the other detection system. To accomplish this, the gauge 10 includes a first radiation detector 18A and a second pair of radiation detectors 18B, wherein the first radiation detector 18A is located in closer spatial proximity to the radiation source 22. The radiation detectors, 18A and 18B, for example, may be any type of gamma ray radiation detector. For instance, the radiation detectors, 18A and 18B, can include preferably Geiger Mueller tubes, but can also include scintillation detectors, or proportional counters. The radiation detectors, 18A and 18B, can be located adjacent to the base 12B of the gauge housing 12. The gauge 10 can also include a moisture detector 16 that can use to measure the moisture of such construction material.

The gauge 10 can also include a handle 50 that is secured to the source rod 20 for vertically extending and retracting the source rod 20. The handle 50 along with a guide and sealing system 70 facilitate the guidance of the source rod 20 through the vertical conduit 32 created by the vertical channel 34 in the tower 30 and the vertical cavity 14 in the base 12B of the gauge housing 12. The handle 50 can be used to move the source rod to a plurality of predetermined source rod locations so as to change the spatial relationship between the radiation source and the at least one radiation detector. The handle 50 includes a coarse adjustment mechanism 52 and a fine adjustment element 54 for adjusting the height of the source rod 20 for positioning the radiation source 22 relative to the radiation detectors 18A, 18B to provide proper measurement at the different predetermined source rod locations. In particular, the source location at backscatter is extremely important and should be very precise.

To provide the predetermined source rod locations, an indexing mechanism can be provided. For example, as shown in FIGS. 2-6, an index positioning strip 80 can be placed in the tower 30 that can be engaged by the handle 50 to hold the source rod 20 at a predetermined source rod location. The index positioning strip 80 can include index holes 82 therein. The index holes 82 can serve as notches that the handle 50 engages as will be explained in more detail below. The index holes 82 can be uniformly spaced apart from each other. For example, the index holes 82 can be spaced apart at interval distances of about one inch, about two inches or about three inches.

The tower 30 can include an indexing groove 36 that is adjacent and opens into the vertical channel 34. The index positioning strip 80 can be secured in the indexing groove 36. The index positioning strip 80 can have apertures 84 for accepting fasteners 84, such as screws, rivets or the like that engage the tower 30. The index positioning strip 80 having index holes 82 therein can be securable at a designated location within the vertical channel 34 of the tower 30 to create the notches. Further, the index positioning strip 80 can be adjustable within the tower 30.

A depth strip 100, as shown in FIGS. 9-12, can be positioned in the tower 30 and can provide a non-contact measurement of the source position. The depth strip can use optical sensors, such as optical range finder sensors, acoustic sensors, magnetic sensors and the like to provide non-contact measuring of the positioning of the source rod. The depth strip 100 can include a parting line 100A with the depth strip 100 being convertible from a 12-inch unit to an 8-inch unit along the parting line 10A. Another parting line can be included on the depth strip to create a depth strip that can be used in a backscatter only gauge. To house the depth strip 100, the tower 30 can include a measurement compartment 38. Depending on the type of depth strip 100, the measurement compartment 38 can be a separate channel or passageway for housing the depth strip.

The gauge 10 also includes a radiation shield assembly 90 as shown in FIGS. 2 and 17-24. The radiation shield assembly 90 includes a safety shield 92 that is coaxially mounted in the base 12B of the gauge housing. The safety shield 92 helps to define the vertical cavity 14 in the base 12B of the gauge housing 12. For example, the base 12B is formed to create a shield housing 12D through which an opening passes. The safety shield 92 has a passage 92A passing therethrough. The safety shield 92 fits into the shield housing 12D so that the opening in the shield housing 12D aligns with the passage 92A in the safety shield 92. A set screw 93 can secure the safety shield 92 in place by screwing the set screw 93 into a screw hole 93A in the shield housing 12D. The aligned opening in the shield housing 12D and the passage 92A through the safety shield 92 can create the vertical cavity 14.

Figure 21:
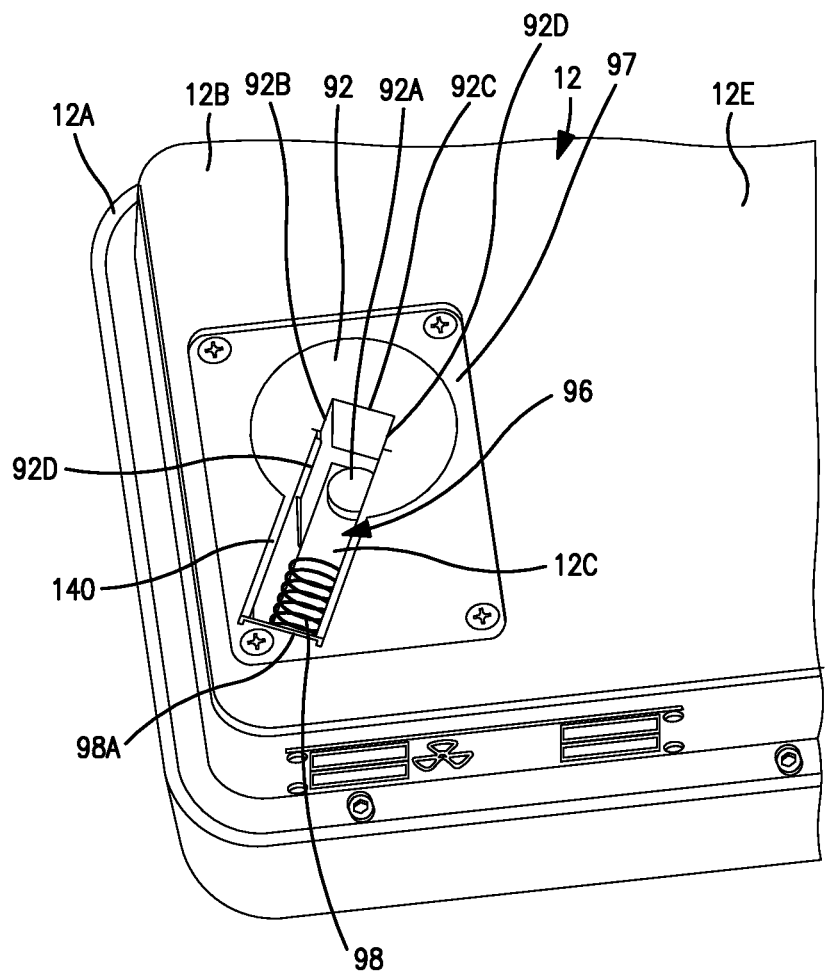

The radiation shield assembly 90 also includes a sliding block 94 that is positionable to move laterally between two positions relative to the safety shield 92. The sliding block 94 can reside in a first position blocking a distal end of the vertical cavity 14 such that radiation is shielded from exiting the cavity. The sliding block 94 can also reside in a second position adjacent to the vertical cavity. In the second position the source rod 20 can move vertically through the radiation shield assembly 90 and the base 12B of the gauge housing 12. The base 12B of the gauge housing 12 and the safety shield 92 can define a track 96 configured to receive the sliding block 94 and guide movement of the sliding block 94. For example, a shield track segment 92B can be defined in the safety shield 92 that comprises at least a portion of the track 96. The shield track segment 92B and the passage 92A can intersect and merge at the lower end of the safety shield 92 as shown in FIG. 21.

Figure 22:
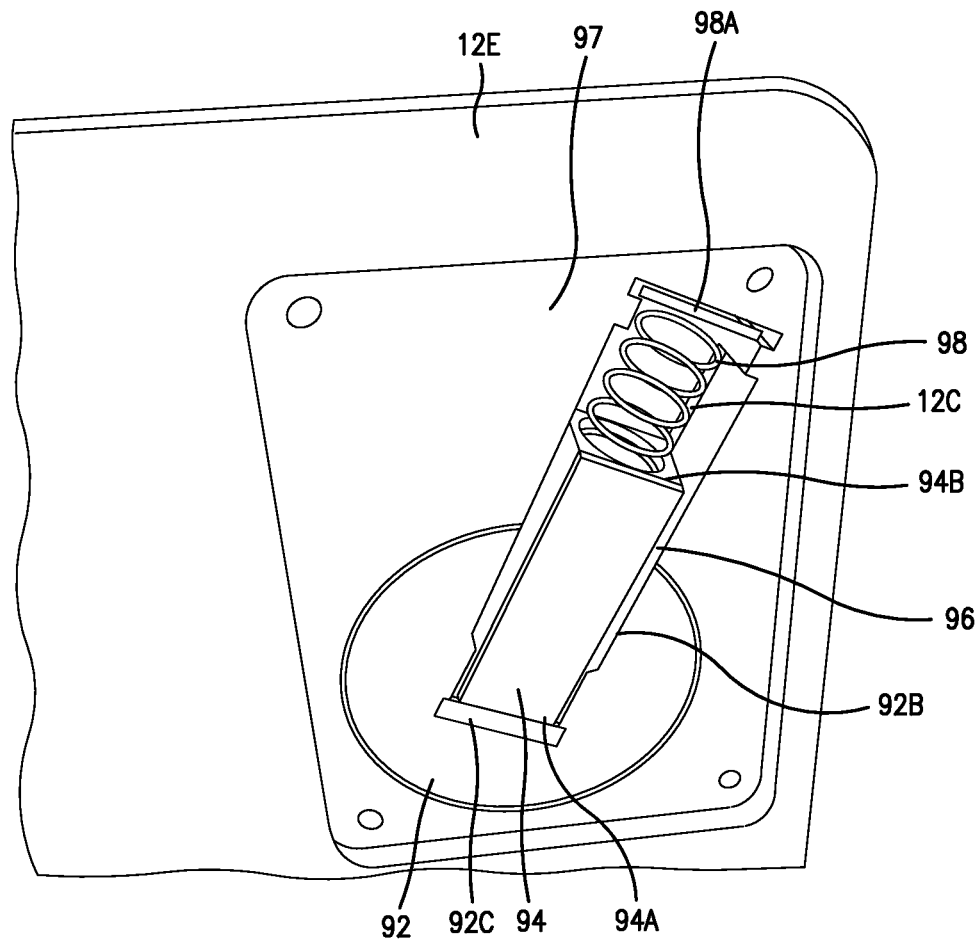
Figure 23:
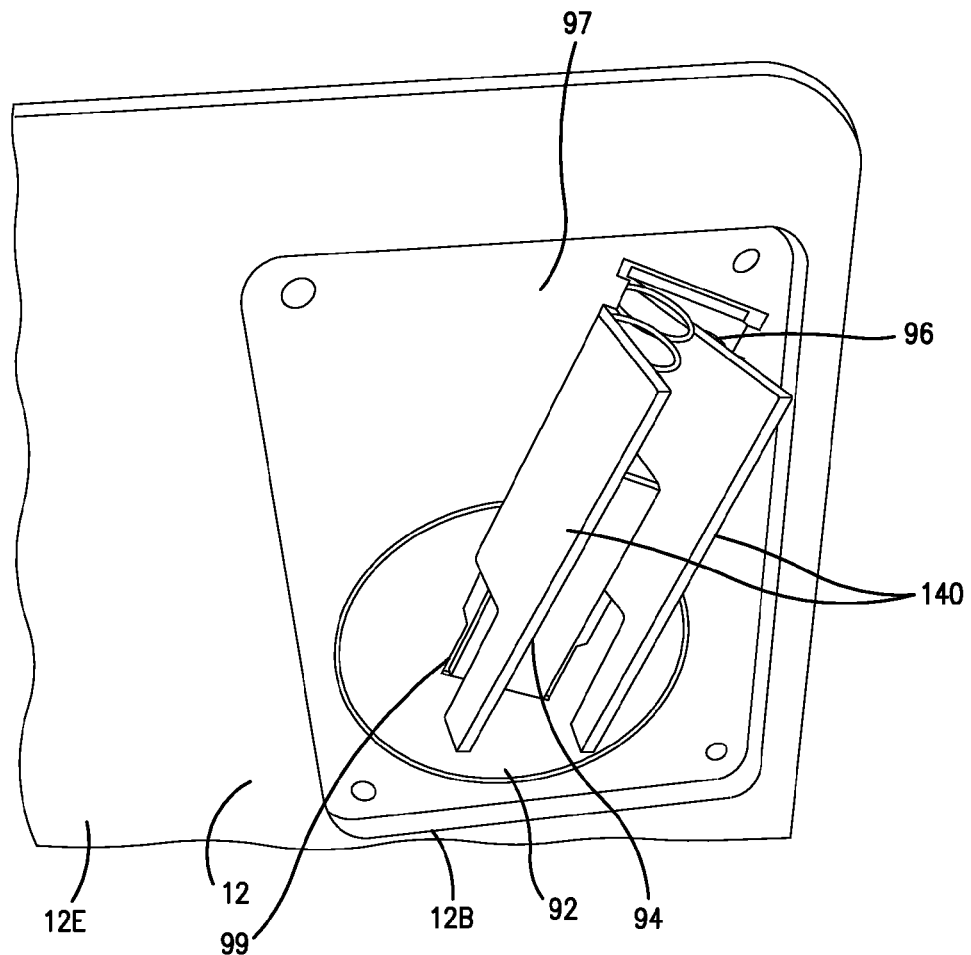

The base 12B of the gauge housing 12 can include a base track segment 12C. The base track segment 12C and the shield track segment 92B can be aligned to form the track 96. The sliding block 94 can be placed in the track 96 formed by the base track segment 12C and the shield track segment 92B. In the first position of the sliding block 94, the sliding block 94 extends through the shield track segment 92B such that an end 94A of the sliding block abuts against an interior wall 92C of the safety shield 92 as shown in FIG. 22. The portion of the interior wall 92C that the sliding block 94 abuts can comprise a hardened material, such as hardened steel, as will be explained in more detail below. In this first position the vertical cavity 14 and the vertical conduit 32 which it partially forms are closed by the sliding block 94, thereby blocking radiation. In the second position of the sliding block 94, the end 94A of the sliding block 94 is moved away from the interior wall 92C of the safety shield 92 so that the vertical cavity 14 and the vertical conduit 32 which it partially forms are opened so that the source rod 20 can emerge. In such a position, the sliding block 94 is adjacent the vertical cavity 14.

A spring 98 can engage the sliding block 94 to bias the sliding block 94 into the first position. The spring 98 can engage the end 94B of the sliding block 94. Further, base 12 can include a spring guide 98A. The spring 98 can reside between the spring guide 98A and the end 94B of the sliding block 94.

As shown in FIG. 2, the safety shield 90 and sliding block 94 of the radiation shield assembly 90 are operatively positioned to minimize the user's exposure to radiation when the radiation source 22 is in the safe position. The safety shield 90 can be constructed of lead or tungsten. However, other radiation shielding material may be used. The sliding block 94 can also comprise radiation shielding material such as tungsten.

The gauge 10 can include a remote user interface that can be used to initiate a measurement of the gauge 10 in addition to the user interface 13 on the gauge housing 12. For example, the remote user interface can be a remote keypad 120 as shown in FIGS. 1-3 and 25B. The remote keypad 120 can be located on a top of the tower 30 and distal from the gauge housing 12. The remote keypad 120 can comprise multiple switch states. The states can include a start switch 122 and an escape switch 124. The start switch 122 can be used to begin a gauge count or other tests once the gauge 10 and source rod 20 are in a proper position. The escape switch 124 can be used to abort such tests. The tower 30 can include a routing compartment 39 for routing the electrical wiring for the second keypad 120 into the gauge housing 12 for connection with the CPU 17. The routing compartment 39 can be a separate channel or a passageway within the tower 30. Alternatively, the remote keypad can be a wireless control mechanism, such as a fob, which is physically separated from the gauge 10 and is in wireless communication with the gauge 10.

An embodiment of the tower 30, handle 50, radiation shield assembly 90 and other related features will now be described in more detail. The tower, or source rod housing, 30 as shown in FIGS. 1-8 provides sturdiness and durability to protect the source rod 20. The tower 30 can substantially surround the source rod 20. The tower 30 provides a structure that supports the source rod 20 and limits the amount of stress placed on the source rod 20 that can occur by an unintended clockwise or counterclockwise torque. Such torque can occur when the source rod 20 is in a safe position. Thereby, the tower 30 provides a stiffer source rod 20 positioning as compared to gauges without a tower. The tower 30 can have any cross-sectional shape. For example, the tower 30 may have a cross-section that is circular, square, rectangular or the like. Further, as shown in the Figures, the tower 30 can have a triangular cross-section. The tower 30 can comprise a metal or a hardened plastic. For example, the tower 30 can be extruded aluminum.

Figure 4A:
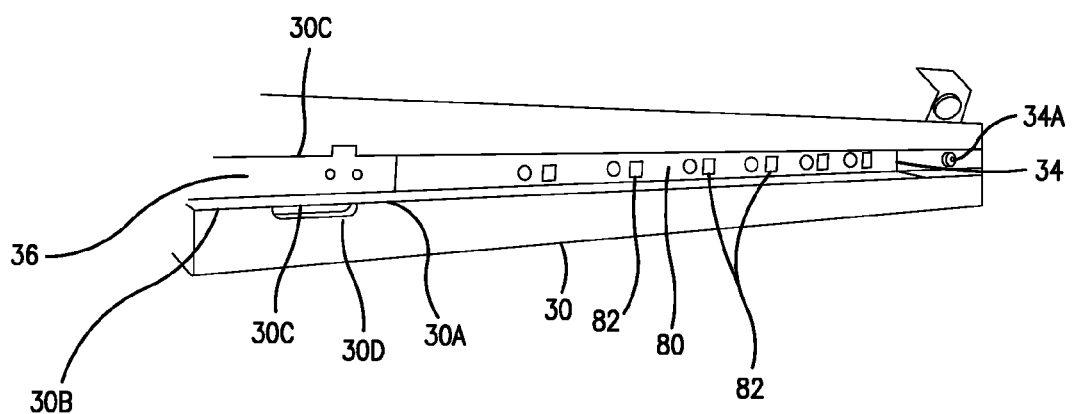
FIG. 4A illustrates a perspective view of an embodiment of a support tower, or source rod housing, used in a nuclear gauge according to the present subject matter.
Figure 4B:
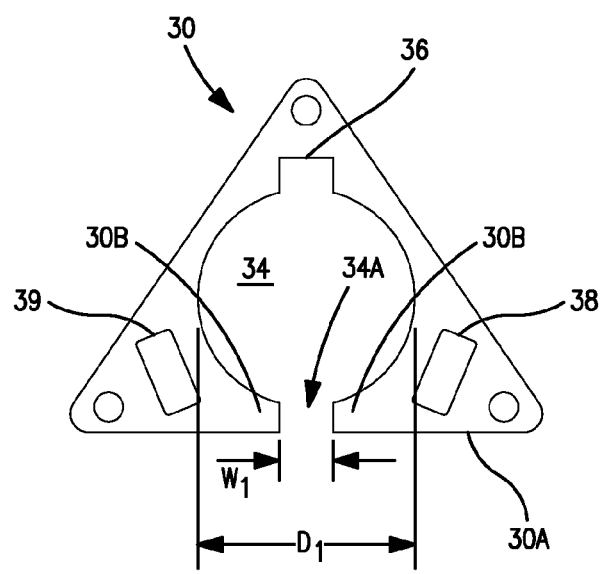
FIG. 4B illustrates a horizontal cross-sectional view of the support tower illustrated in FIG. 4A.

The channel 34 in tower 30 is wide enough to provide sufficient clearance for the source rod. For example, as shown in FIG. 4B, the channel 34 can have a circular cross-sectional diameter $D_1$ that provides easy movement of the source rod 20 therein. The channel 34 can have an inlet 34A that is formed by edges 30B and opens to a side 30A of the tower 30. The handle 50 affixed to the source rod 20 can be configured to slidably engage the inlet 34A. Handle 50 can have a grip portion 50A that extends outward from the tower 30, an engagement portion 50B that is adjustably connected the source rod 20 and a neck portion 50C that is disposed between the grip portion 50A and the engagement portion 50B. The inlet 34A can have a width $W_1$ in which the neck portion 50C can reside. The width $W_1$ of inlet 34A can be less than the diameter or width of the source rod 20.

Figure 13A:
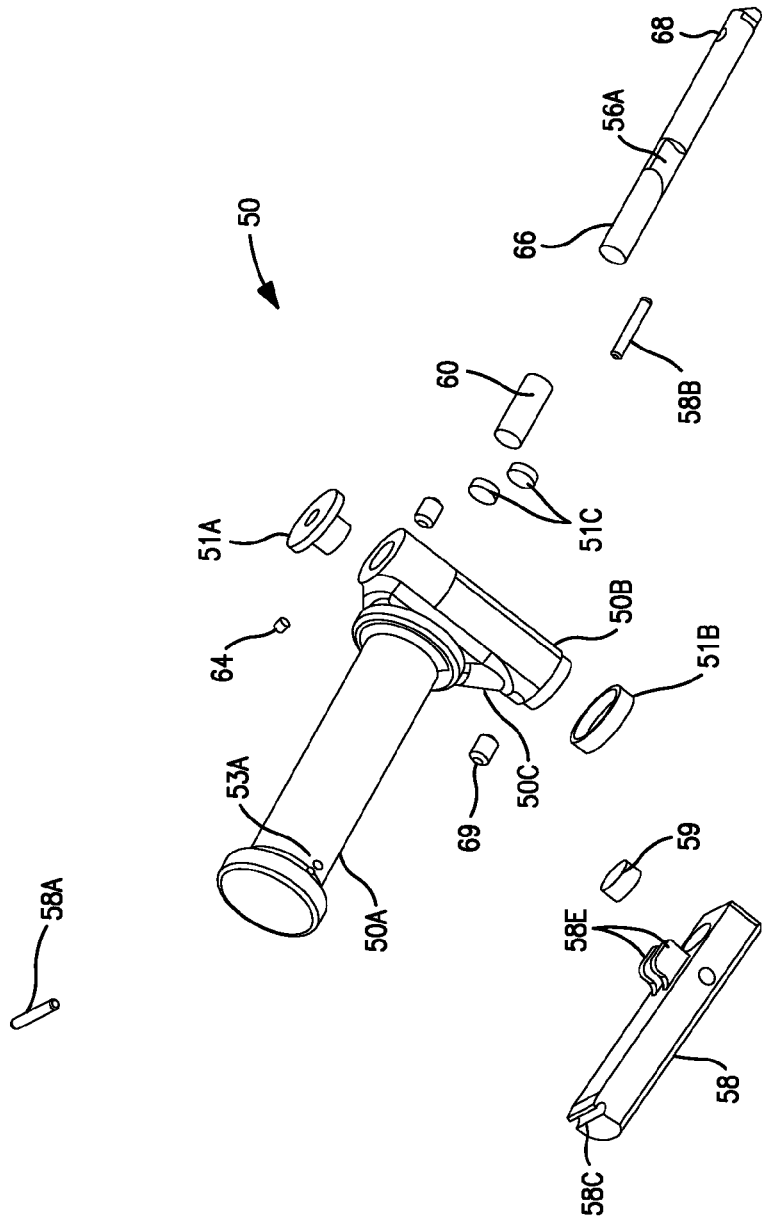
FIGS. 13A-13C illustrate exploded views of an embodiment of a handle used in a nuclear gauge according to the present subject matter.
Figure 13D:
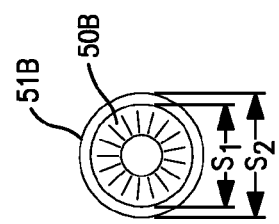
FIG. 13D illustrates horizontal cross-sectional view of the handle illustrated in FIG. 13A.
Figure 13B:
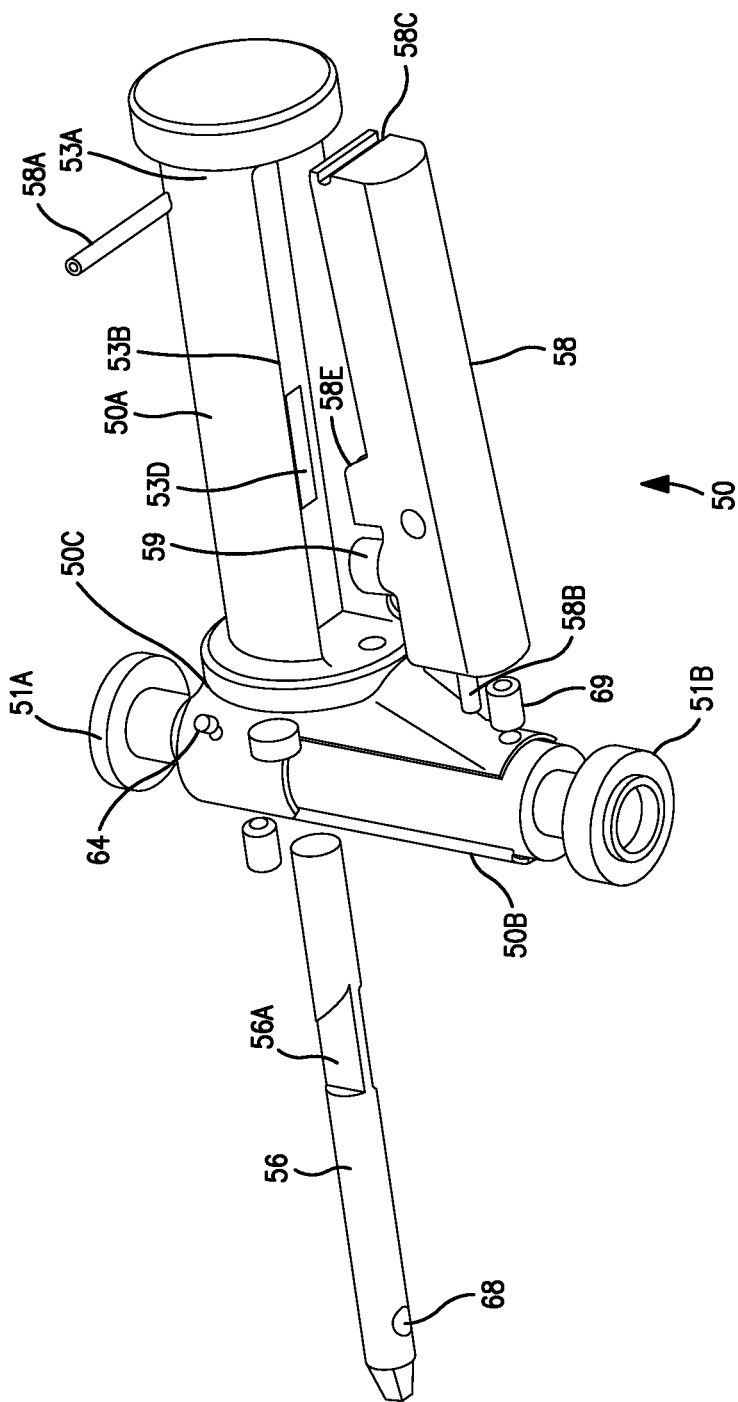
Figure 13C:
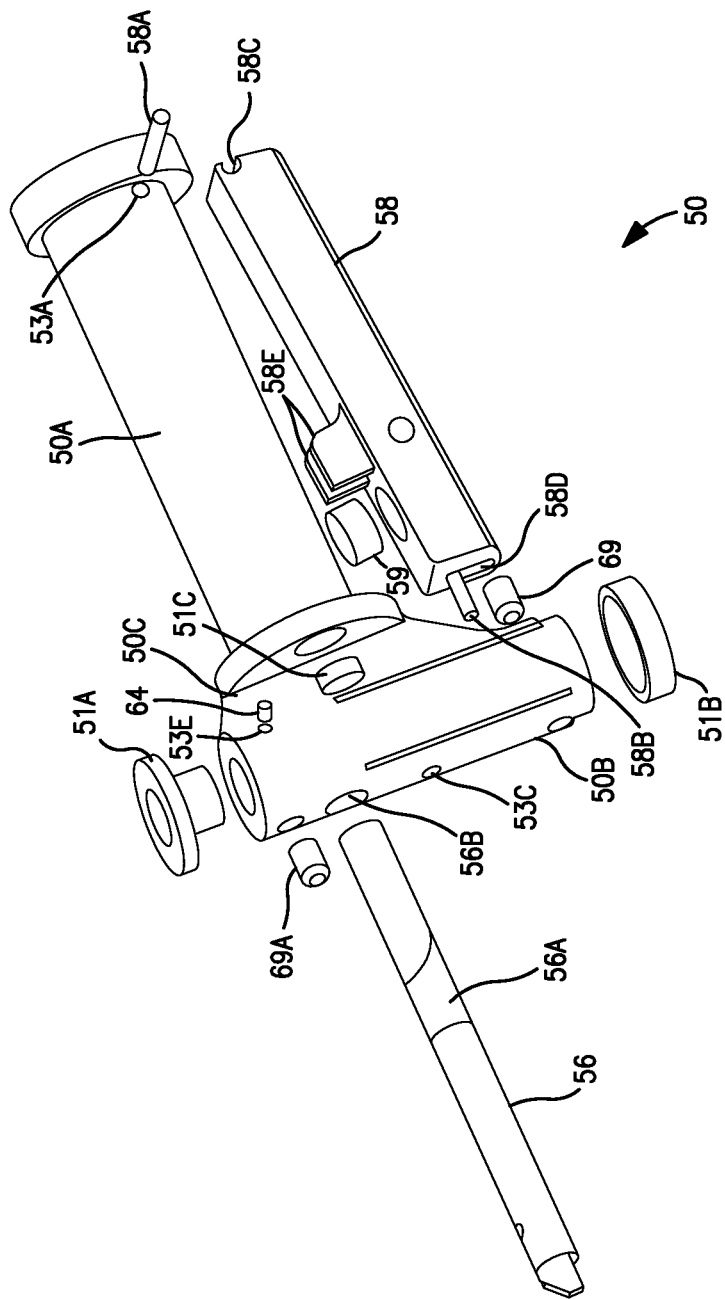

The engagement portion 50B can be configured to slidably engage the channel 34. For example, the handle 50 can include slider pads 51C and/or at least one slider disc as shown in FIG. 13C. In the embodiment shown in FIGS. 13A-13D, a top slider disc 51A and a bottom slider disc 51B are provided that are positioned on either end of the engagement portion 50B of the handle 50. The slider discs 51A, 51B can have a cross-sectional shape taken in a plane parallel to the grip portion 50A of the slider discs 51A, 51B that is larger than the cross-sectional shape of the engagement portion 50B. For example, the cross-sectional view of the engagement portion 50B below the grip portion 50A and the neck portion 50C illustrated in FIG. 13D shows the outer diameter $S_2$ of the of the bottom slider disc 51A being larger than the outer diameter $S_1$ of the engagement portion 50B. The cross-sectional shapes of the top and bottom slider discs 51A, 51B can be approximately the same size. For example, the outer diameters of the top and bottom slider discs 51A, 51B can be equal. The outer diameters of the top and bottom slider discs 51A, 51B can be similar in size to the diameter $D_1$ of the vertical channel 34 of the tower 30. Thereby, the slider discs 51A, 51B can enhance the stability of the source rod 20 in the vertical channel 34 of the tower 30 and can assist in reducing radial movement of the source rod 20 at the end engaged by the handle 50.

The slider discs 51A, 51B can be at least partially formed from a friction reducing material. For instance, the slider discs 51A, 51B can have an outer perimeter that interfaces with the tower 30 in the vertical channel 34 that is a friction reducing material. For example, the slider discs 51A, 51B can be or can include a polymer having a low coefficient of friction. The polymer can be at least one of polytetrafluoroethylene, perfluoroalkoxy, and fluorinated ethylene propylene.

The handle 50 can include a plunger 56 and a trigger 58. The plunger 56 can be extendable to engage index holes 82 of the index positioning strip 80 disposed within the tower 30 and retractable to disengage the index holes 82 by actuation of the trigger 58. The trigger 58 can be located on the underside of the grip portion 50A of the handle 50. The trigger 58 can be held in place by a pair of pins 58A, 58B. The end of the trigger 58 distal from the neck portion 50C of the handle 50 can have a pivot groove 58C that engages pivot pin 58A to create a pivot point for the trigger 58. The pivot pin 58A can reside in the pivot aperture 53A defined in the grip portion 50A. The trigger 58 can include a vertical extending slot 58D as shown in FIGS. 2 and 13C that can engage locking pin 58B. The slot 58D permits the trigger 58 to be moved up and down with the pin 58B residing in the slot 58D. A trigger spring 59 can engage the trigger 58 at a position on the trigger closer to the slot 58D and more distal from the groove 58C. The trigger spring 59 biases the trigger 58 away from the plunger 56. The handle 50 can also include a spring 60 that engages the plunger 56 and a spring guide 62 within the grip portion 50A. The spring 60 biases the plunger 56 towards an extended position.

The trigger 58 can include at least one protrusion 58E that engages at least one retraction groove 56A on the plunger 56. In the embodiment shown, two protrusions 58E are provided on the trigger 58 and two retraction grooves 56A are provided on the plunger 56. However, it is understood that one or more protrusions and corresponding retraction grooves may be provided.

The protrusions 58E can be slanted to match a slant in the groove 56A. The slant of the protrusions 58E and the retraction grooves 56A are such that, as the trigger 58 is squeezed upward, the protrusions 58E engage the retraction grooves 56A forcing the plunger 56 to a retracted position. Once the source rod is moved to one of the predetermined source rod locations that is aligned with a corresponding index hole 82, the trigger 58 can be released. The trigger spring 59 biases the trigger 58 away from the plunger 56 and the spring 60 biases the plunger 56 towards an extended position with the plunger 56 engaging the corresponding index hole 82.

Figure 5:
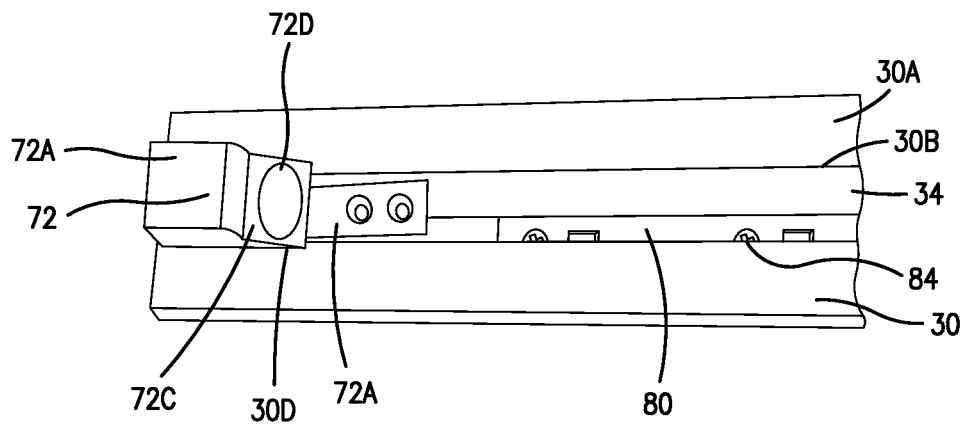
FIG. 5 illustrates a close-up perspective view of the support tower illustrated in FIG. 4A.
Figure 6:
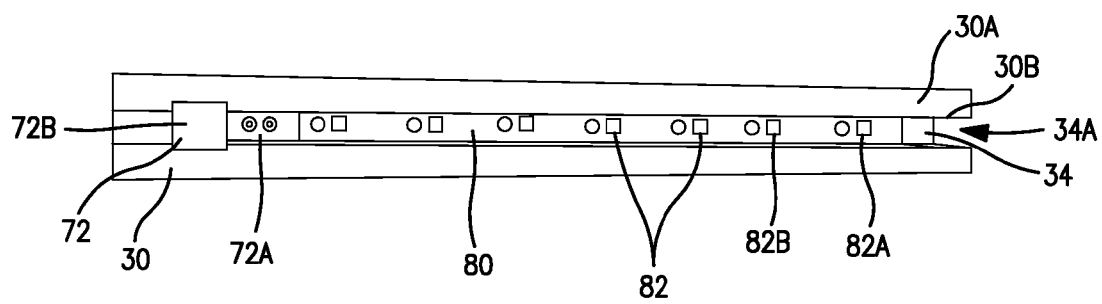
FIG. 6 illustrates a perspective view of the support tower illustrated in FIG. 4A.
Figure 7A:
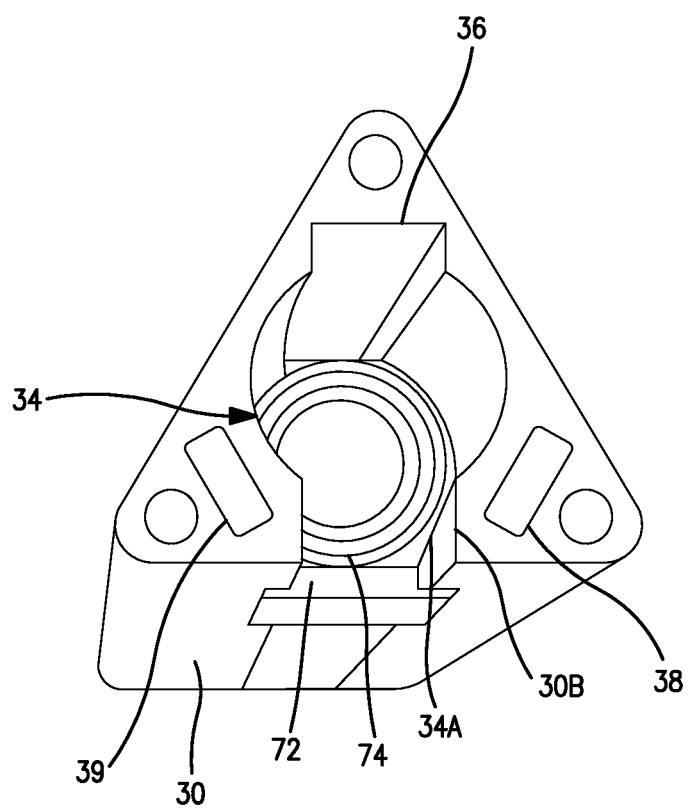
FIG. 7A illustrates a perspective end view of the support tower illustrated in FIG. 4A.
Figure 7B:
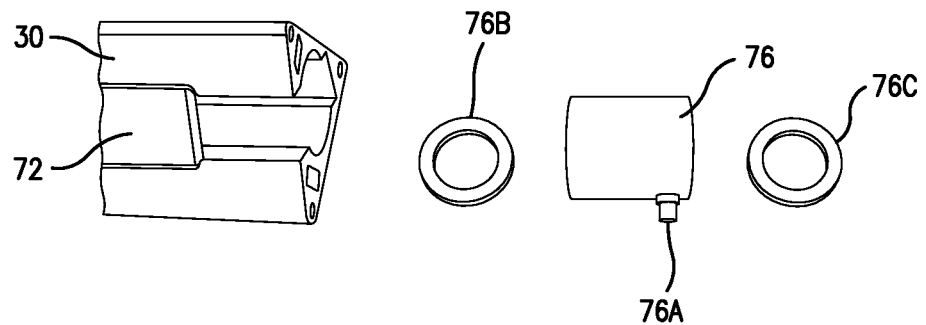
FIG. 7B illustrates a perspective view of the support tower illustrated in FIG. 4A and an embodiment of a tube spacer to be inserted into the tower according to the present subject matter.
Figure 7C:
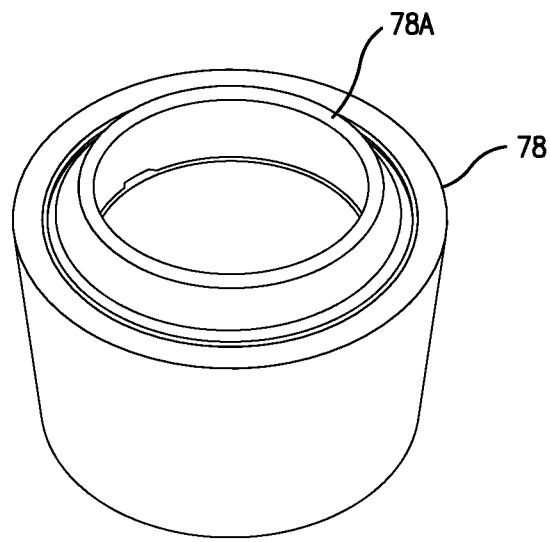
FIG. 7C illustrates a perspective view of an embodiment of a source rod bearing to be inserted into a support tower, or source rod housing, according to the present subject matter.
Figure 8:
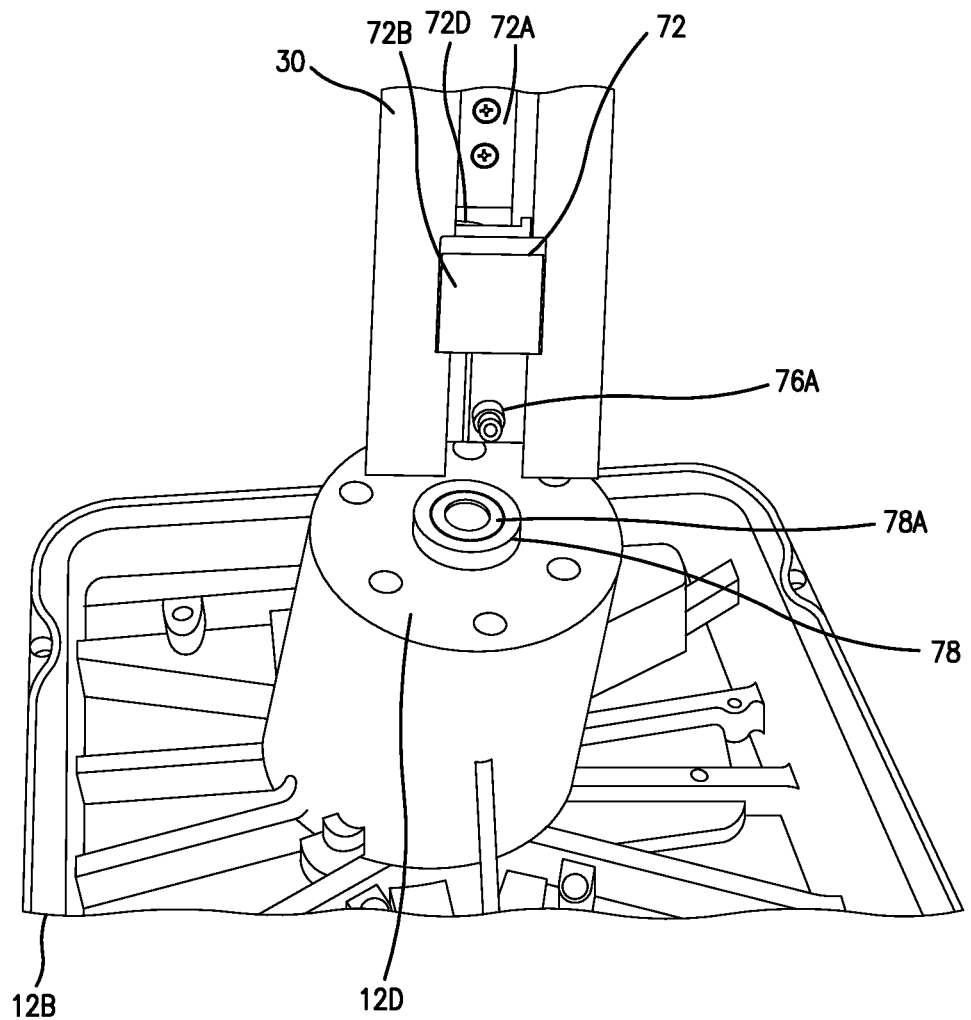
FIG. 8 illustrates a perspective view of an embodiment of a support tower, or source rod housing, and base of a gauge housing according to the present subject matter.

The index holes 82 of the index positioning strip 80 can provide different source rod locations by holding the source rod 20 at different positions as shown in FIGS. 2-6. These locations can include, for example, index hole 82A as shown in FIG. 6 that corresponds to the "safe" position wherein the radiation source 22 is raised and shielded from the test material. The safe position is used to determine the standard count. Another index hole 82B corresponds to the backscatter mode wherein the radiation source 22 is located adjacent to the surface of the test material underlying the gauge 10. Other index holes 82 can correspond to a plurality of direct transmission positions. The use of the index positioning strip 80 with its adjustability permits less stringent manufacturing tolerances. Therefore, the index positioning strips 80 allow greater variability with this design. Thus, the position of the strip 80 can be adjusted for additional manufacturing flexibility. The strip 80 can be attached in different manners. For example, the tower 30 can include adjustment screw holes 36A (see FIG. 2) that can align with apertures 84 in strip 80 for insertion of screws. Thus, adjustment screw holes 36A and apertures 84 can be used to secure the strip 80 to the tower 30. The index positioning strip 80 can be convertible to a length that can be used with a 12-inch source rod, an 8-inch, or to a length that is usable with a backscatter only gauge.

The safe position corresponding to the index holes 82A can position the tip of the source rod 20 at least about 2.20 inches above the outer surface of the base 12B of the gauge housing 12. This places the radiation source 22 in a position that exhibits reduced sensitivity of the standard count to slight radiation source positioning variability in the vertical direction. Specifically, the radiation standard count rate with the radiation source 22 in the safe position changes only about 2-10 scaled counts per mil of radiation source position change in the vertical direction in the gauge 10.

Figure 9:
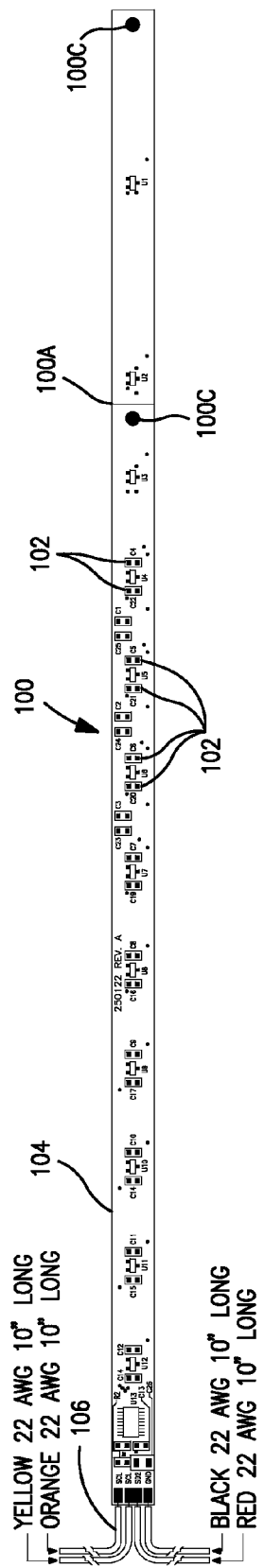
FIG. 9 illustrates a plan view of an embodiment of a depth strip that can provide a non-contact measurement in a nuclear gauge according to the present subject matter.
Figure 10:
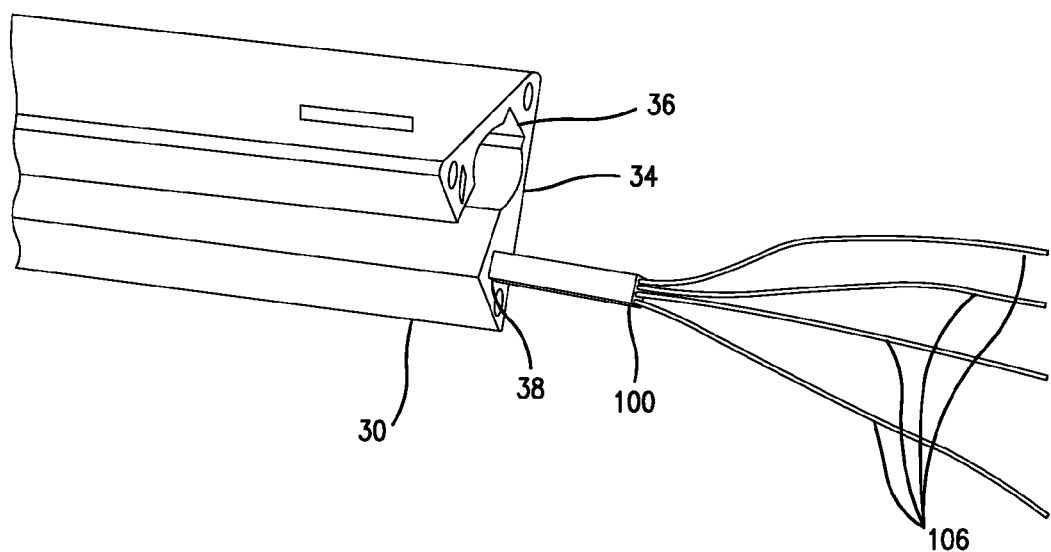
FIG. 10 illustrates a perspective view of an embodiment of a support tower, or source rod housing, and depth strip according to the present subject matter.
Figure 11:
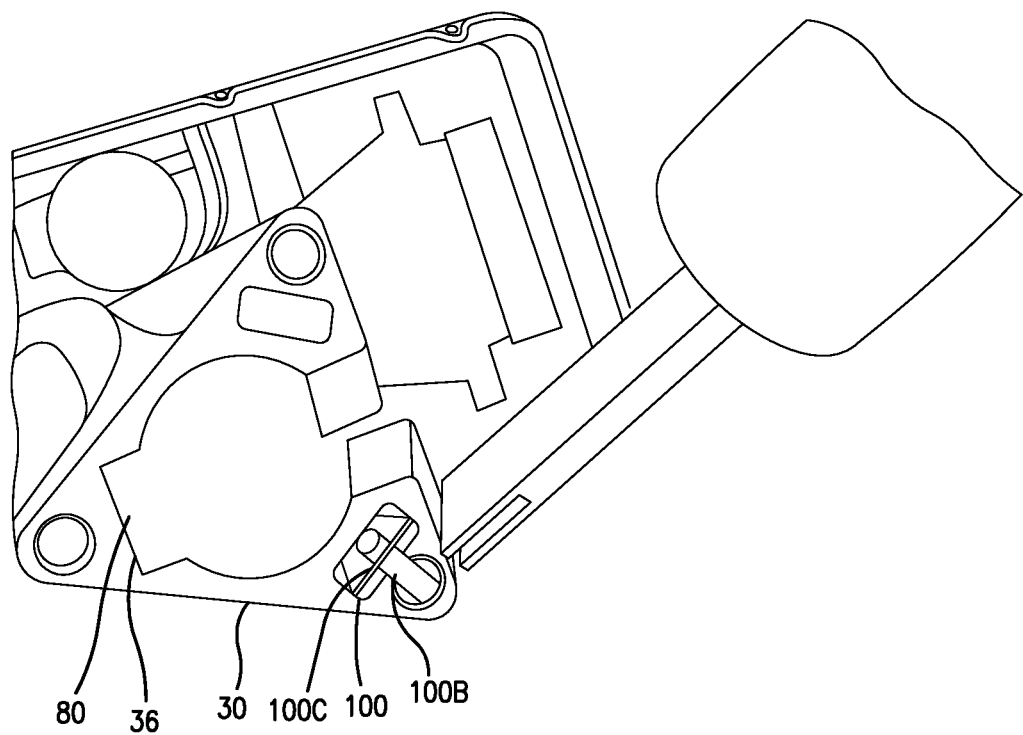
FIG. 11 illustrates a perspective end view of the support tower and depth strip illustrated in FIG. 10.

As illustrated in FIGS. 9-11, a depth strip 100 can be positioned in the tower 50 and can provide non-contact measurements used to determine the depth at which the source rod 20 is positioned during use. For example, the tower 50 can include a measurement compartment 38 in which the depth strip 100 can be placed. The measurement compartment 38 can be a channel or groove. Alternatively, the compartment 38 can be a passageway within the tower 30 in proximity to the vertical channel 34 in which the source rod 20 resides. As stated above, the depth strip can use optical sensors, such as optical range finder sensors, acoustic sensors, magnetic sensors and the like to provide non-contact measuring of the positioning of the source rod.

As described above, the depth strip 100 that resides in the measurement compartment 38 can be a sensor that uses magnetically actuated, low power Hall Effect sensors 102 as the means to determine the rod position. For example, the Hall Effect sensors 102 of the depth strip 100 can be alignable with the index holes 82 of the index positioning strip 80. The Hall Effect sensors 102 can be mounted on a printed circuit board 104 at discrete positions which are spaced about one inch and/or about two inches apart. The printed circuit board 104 can include other electronics to power the Hall Effect sensors 102, determine which Hall Effect sensor 102 is activated, and communicate this information with the gauge CPU 17 that is in communication with the user interface 13. This configuration allows for absolute location of the source rod, not just relative to the safe position.

The handle 50 can include a magnet 64 thereon that is detectable by the Hall Effect sensors 102 to provide non-contact measuring of the positioning of the source rod 20. The Hall Effect sensors 102 can be placed on the printed circuit board 104 so that they will line up with the magnet 64 located on the handle 50 of the moveable source rod 20. The source rod 20 can be then "indexed", such that it can only be placed in discrete positions through the use of the index positioning strip 80. These positions can be about one inch or about two inches apart. Special indexing is also achievable by replacing the strip. At each of these discrete positions, the magnet 64 in the handle 50 can be positioned directly across from one of the Hall Effect sensors 102 on the printed circuit board 104.

Thus, only one of the Hall Effect sensors 102 is actuated at a time. When the user starts a gauge operation that is source rod position sensitive, the CPU 17 can communicate with the printed circuit board 104 electronics to determine which Hall Effect sensor 102 is activated. The CPU 17 software can be structured such that it can relate the actuated Hall Effect sensor 102 to a known index position. If a Hall Effect sensor 102 is not actuated, the CPU 17 can inform the gauge user that the source rod 20 is not in a valid position. If a Hall Effect sensor 102 is actuated, the CPU 17 can start the gauge operation, and pass the index position to the software. In this manner, the gauge user does not have to manually enter the source rod position.

By including a parting line 100A along the printed circuit board 104, the depth strip 100 is convertible from a 12-inch unit to an 8-inch unit along the parting line. In this manner, a single designed depth strip 100 can be used in different gauges 10 that have two different distances at which the source rod 20 can extend.

To facilitate proper movement of the source rod 20 within the vertical conduit 32 formed by the vertical channel 34 in the tower 30 and the vertical cavity 14 in the gauge housing 12, the guide and sealing system 70 can be provided. The guide and sealing system 70, as shown in FIGS. 1, 2 and 4-8, can work in conjunction with the at least one slider disc on the handle 50, such as slider discs 51A, 51B, to increase stability and minimize radial movement of the source rod 20. The guide and sealing system 70 can include a bracket 72 that can be placed and secured in the vertical channel 34 of the tower.

The bracket 72 can have a first end portion 72A that is configured to lie flat within the groove 36 in the tower 30. The first end 72A portion can be secured below the index positioning strip 80, but aligned with the index positioning strip 80 within the groove 36. The bracket 72 can also have a second end portion 72B that is configured to reside outside of the channel 34 of the tower 30. For example, as shown in FIGS. 4-6, the second end portion 72B can be wider than the width $W_1$ of the inlet 34. The tower 30 can have a groove 30C cut into each of the edges 30B on either side of the inlet 34A of the channel 34. The second end portion 72B can be configured to reside in the grooves 30C. The second end portion 72B can extend substantially parallel to the first end portion 72A of the bracket 72. Between the first end portion 72A and the second end portion 72B, the bracket 72 can include a mid-portion 72C. The mid-portion 72C can be substantially perpendicular to both the first end portion 72A and the second end portion 72B and also about perpendicular to the vertical channel 34 in which the source rod is disposable. The mid-portion 72C includes a bracket aperture 72D through which the source rod can pass. The edges 30B can also include slots 30D through which the bracket 72 including the mid-portion 72 can pass so that when the bracket 72 is secured in the tower 30, the first end portion 72A resides within the groove 36, the second end portion 72B resides within the grooves 30C, and the mid-portion 72B extends through the slots 30D and into the vertical channel 34 so that the bracket aperture 72D aligns with the vertical channel 34 to accept the passage of the source rod 20 therethrough.

The guide and sealing system 70 (see FIG. 2) can also include an upper seal 74 that can be placed into the vertical channel 34 below the bracket 72 so that the upper seal abuts against the underside of the mid-portion 72C of the bracket. The upper seal 74 can have an inner diameter that is less than the diameter of the bracket aperture 72D and is in close tolerance of the source rod 20. The outer diameter of the upper seal 74 can be substantially similar to the diameter $D_1$ of the vertical channel 34. After the upper seal 74 is seated against the bracket 72, a tube spacer 76 with a grease fitting 76A can be seated against the upper seal 74. The guide and sealing system 70 can also include a source bearing 78 that can be secured against the tube spacer 76 at the end distal from the bracket 72 and upper seal 74. The source rod bearing 78 can include a seal wiper 78A that acts as a lower seal. The source rod bearing 78 can be seated in the shield housing 12D of the base 12B above the radiation shield assembly 90. The tube spacer 76 can include a top washer 76B and a bottom washer 76C that can be placed on either end of the tube spacer. For example, top washer 76B can be placed on the end of the tube spacer 76 proximate to the upper seal 74 and the bottom washer 76C can be placed at the end of the tube spacer 76 proximate to the source rod bearing 78. The source rod bearing 78 can be a bushing. The source rod bearing 78 can guide the source rod 20 through cavity 14 in the gauge housing 12 with an extremely close fit to the source rod 20 in order to minimize variability in radiation source positioning. Specifically, the outer diameter of source rod bearing 78 can be about 1.1265 inches +/− about 0.0005 of an inch and the bearing inner diameter can be about 0.6265 of an inch +/− about 0.0005 of an inch. Additionally, the bearing housing diameter can be about 1.1265 inches +/−0.0005 of an inch. The source rod 20 diameter can be about 0.625 of an inch +/− about 0.001 of an inch. This results in a nominal bearing clearance of about 0.00025 of an inch and a bearing clearance range of press-fit to about 0.001 of an inch. The nominal source rod clearance can be about 0.00175 of an inch and the source rod clearance range can be from about 0.0005 to about 0.0030 of an inch. Thus, the source rod 20 has a total range of radial movement of no more than about 0.0005 of an inch to about 0.0040 of an inch. Since the desired position of the source rod 20 is on the true centerline of the source rod bearing 78, the movement away from true center is actually the radial clearance, which equals one-half of the diametrical clearance. Thus, the maximum movement away from true center of the source rod 20 can be about one-half of 0.0040 of an inch, or 0.0020 of an inch.

It is important to correctly calibrate the height of the source rod 20 to ensure that the source rod 20 will be at the correct depths when the handle engages the index positioning strip 80. To calibrate the gauge 10, the exact source height can be adjusted in real time by the assembly technician using only a screwdriver or a wrench. To calibrate the gauge 10, the exact source height can be adjusted in real time by the assembly technician using only a wrench or a screwdriver. The screwdriver or wrench can be inserted in or onto a threaded device, such as a screw or bolt 54A that is securely affixed to the source rod 20 such that the screw does not rotate separately from the source rod 20. Any type of finely pitched thread device can be used. A screw such as a flathead screw, slotted screw, a Phillips head screw, a star screw such as those sold under the name TORX®, a spline drive screw, hex screw, double hex screw or the like, can be used as the fine adjustment element 54. Similarly, an Allen Head screw can be used.

Access can be permitted to the screwdriver or wrench through the top of the tower 30 and the handle 50. The remote keypad 120 or other top portion is removed. The handle 50 can define at least one adjustment aperture therein to permit access to the fine adjustment element 54. For example, the handle 50 includes adjustment apertures 66 and 68 as shown in FIGS. 2, 13B, and 14 in both the engagement portion 50B and the plunger 56, respectively, so that when the source rod 20 is in backscatter position all the adjustment apertures 66 and 68 in the handle 50 are aligned within reach of the assembly technician's screwdriver or wrench. In the embodiments where the handle 50 can include a plunger 56 and a trigger 58, the plunger 56 can define an adjustment aperture 68 that aligns with the adjustment aperture 66 in the handle 50 when the plunger 56 resides in an extended position.

The coarse adjustment mechanism 52 and fine adjustment element 54, as shown in FIGS. 2 and 14, can be used to set the height of the source rod 20 during manufacturing with the settings being permanent or semi-permanent. "Semi-permanent" as used herein means that the height of the source rod 20 cannot be reset without physical manipulation through the use of chemical and/or mechanical tools. The handle 50 can also include one or more set screws 69 for holding and locking the source rod 20 in place after the height of the source rod 20 is adjusted with the coarse adjustment mechanism 52 and the fine adjustment element 54. The source rod 20 can be in a backscatter position when the height of the source rod 20 is adjusted with the coarse adjustment mechanism 52 and the fine adjustment element 54. This ability greatly reduces assembly time, improves locating precision and repeatability.

Within the handle 50, the coarse adjustment mechanism 52 can include a threaded section 52A and the fine adjustment element 54 can include a screw, such as an Allen Head screw 54A. Such an Allen Head screw 54A can be securely affixed to the source rod 20 such that the screw does not rotate separately from the source rod 20.

The coarse adjustment mechanism 52 permits the quick attachment of the source rod 20 into the handle 50. The fine adjustment element 54 uses the threaded section 52A as well, but fine adjustment element 54 permits for very small incremental movement of the source rod 20 through partial rotation of the source rod 20. The fine adjustment element 54 can permit accurate and acute adjustment of the height of the source rod of less than about one hundredth of an inch. For example, the fine adjustment element 54 can permit adjustment of the source rod 20 to plus or minus about 0.005 of an inch. In some embodiments, the fine adjustment element 54 can permit adjustment of the source rod 20 to plus or minus about 0.001 of an inch. Thus, both coarse adjustments and fine adjustments can be made to the source rod height.

Figure 16:
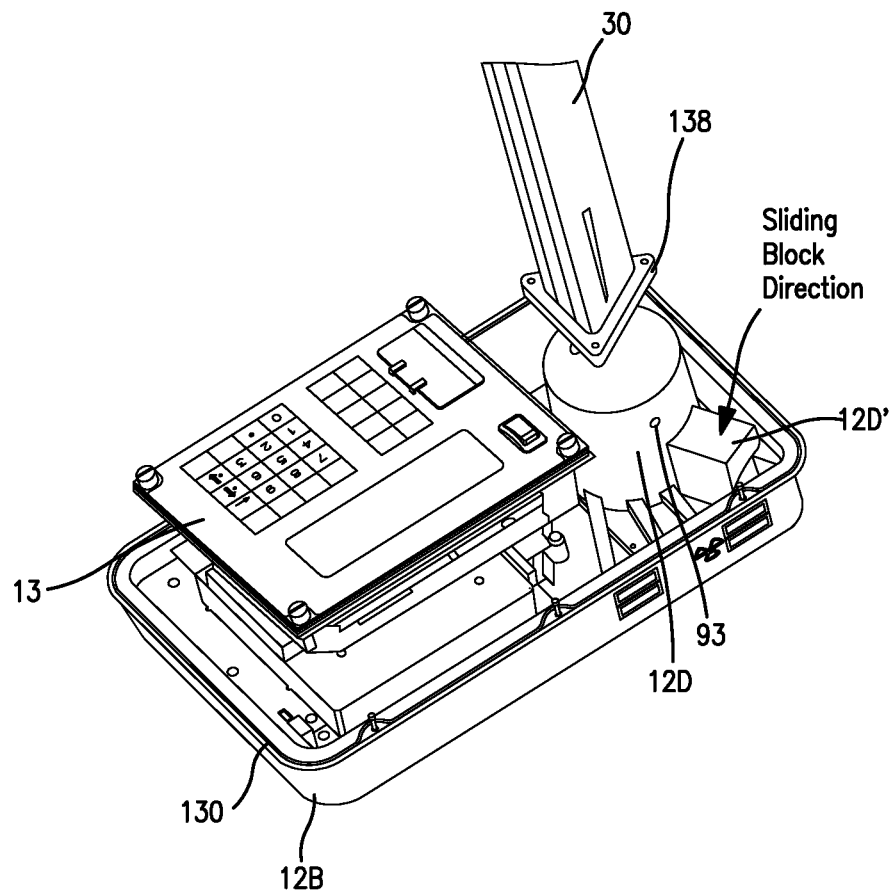
FIG. 16 illustrates a perspective view of an embodiment of a nuclear gauge according to the present subject matter.

In the past, attempts have been made to keep water out of the gauges. Humidity and water can adversely affect the high voltage electronics. The problem has always been to develop a seal that allows the source to move freely up and down while completely blocking elements, such as humidity and moisture. To protect the electronics contained within the gauge housing 12 of the gauge 10, precautions can be taken to ensure a good seal is created between the top cover 12A and the base 12B of the gauge housing 12 and between the tower 30 and the gauge housing 12. For example, as shown in FIG. 16, an O-ring 130 can be positionable in a groove 132 within the base 12B of the gauge housing 12 between the base 12B and the top cover 12A. The O-ring 130 can extend around an outer parameter of the base 12B with the top cover 12A engaging the O-ring 130 to create water proof seal between the top cover 12A and the base 12B.

Further, as shown in FIGS. 2 and 25A-25C, a second O-ring 134 having a diameter which fits tightly around the cross-section of the tower 30 can be positioned at the tower base where the tower 30 is secured to the gauge housing 12. The use of the O-ring 134 and a trim plate 138 that fit around the horizontal cross-sectional shape of the tower 30 and engage the top cover 12A of the gauge housing 12 allows the entire circumference of the sealing area to be water tight. This can be especially important in gauges that are specified for all weather use. For example, the cross-section of the tower 30 can be triangular in shape and the top cover 12A can form a groove 136 around opening 15 into which tower 30 can extend. A triangular trim plate 138 having an outer lip 139 can push the second O-ring 134 against the tower 30 to create a water resistant seal. The trim plate 138 can be placed around the tower base and over this second O-ring 134 and then secured to the gauge housing 12.

The radiation shield assembly 90 is described below in more detail. As stated above, the radiation shield assembly 90 has a portion that is operatively positionable to move laterally between two positions. A first position is provided for blocking a distal end 14A of the vertical cavity 14 of the gauge housing 12 such that radiation is shielded from exiting the cavity 14. A second position adjacent to the vertical cavity 14 is provided for allowing vertical movement of the source rod 20 through the radiation shield assembly 90. As described above, the radiation shield assembly 90 can include a sliding block 94 positionable to move laterally between the first position and the second position. A track 96 can be configured to receive the sliding block 94 and guide movement of the sliding block 94. A spring 98 can engage the sliding block 94 and bias the sliding block 94 into the first position.

A safety shield 92 can be included in the radiation shield assembly 90. The safety shield 92 can include a shield track segment 92B therein that comprises at least a portion of the track 96. The base 12B of the gauge housing 12 can include a base track segment 12C. The base track segment 12C and the shield track segment 92B are alignable to form the track 96.

At least one replaceable sliding guide 140, as shown in FIGS. 17 and 18A-18C, is positionable within the track 96 adjacent the sliding block 94. The at least one replaceable sliding guide 140 is configured to reduce friction as the sliding block 94 moves between the first position and the second position. The at least one replaceable sliding guide 140 can comprise two replaceable sliding guides 140 with each replaceable sliding guide 140 extending over at least a portion of the base track segment 12C and the shield track segment 92B on opposing walls of the track 96.

Figure 17:
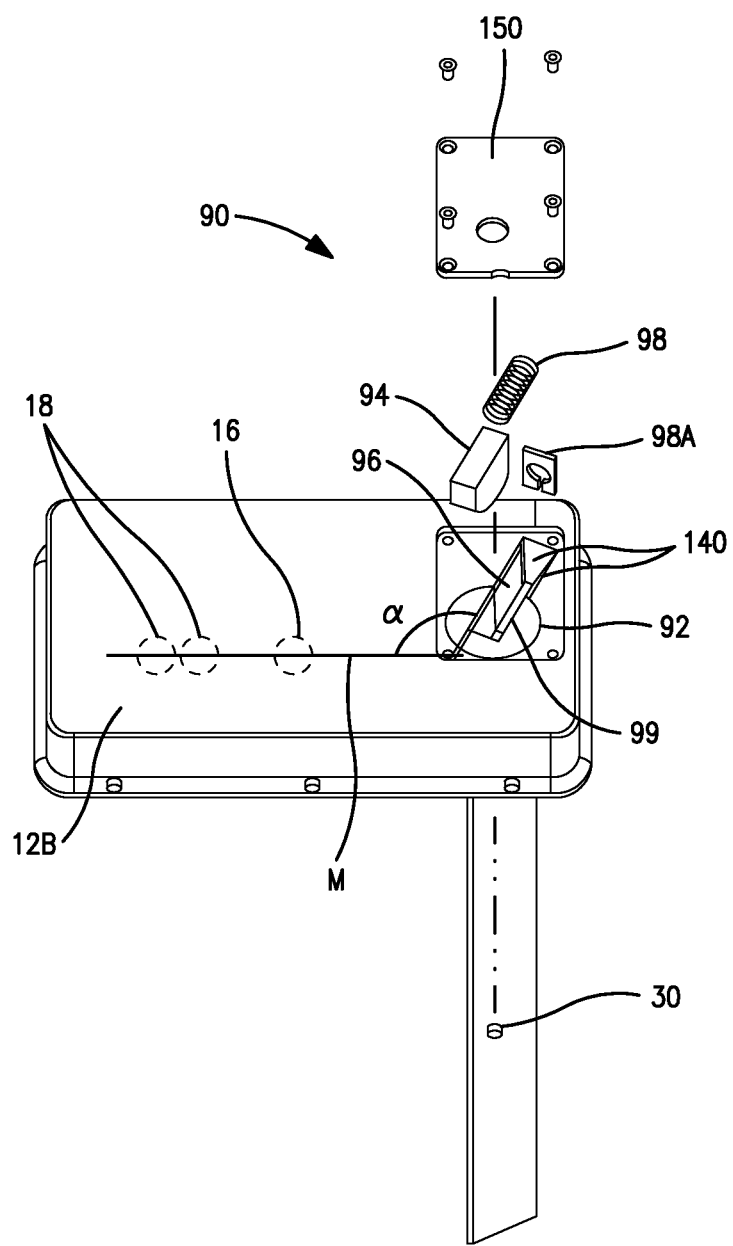
FIG. 17 illustrates a partially exploded bottom view of an embodiment of a nuclear gauge according to the present subject matter.

The track 96 is configured to extend in a direction within the nuclear gauge 10 so that, as the sliding block 94 moves from the first position to the second position, the sliding block 94 moves away from the radiation detector(s) 18A, 18B as shown in FIG. 17 with the sliding block housing 12D'. The track 96 can extend at an angle a of between about 90° and about 180° as measured from a plane M extending between the radiation detector(s) 18A, 18B and the point of the track 96 closest to the radiation detector 18A as shown in FIG. 17. In some embodiments, the track 96 can extend at an angle α of between about 100° and about 135°. The angle α of the track can bias the sliding block 94 toward a closed position due to gravity when the gauge is placed in a carrying case and the carrying case is in its upright position. Further, at such an angle, the effect of the sliding block 94 on the reading of the gauge 10 is minimized as any leakage of radiation is directed away from the detectors.

As stated above, the safety shield can be a molded block. The safety shield 92 can be made of lead. Alternatively, the safety shield 92 can be tungsten or a tungsten and lead mix. For example, the safety shield 92 can comprise concentric cylinders of lead and tungsten. The shield track segment 92B can include two opposing side walls 92D extending into the safety shield 92 and an end wall 92C disposed between the side walls 92D (see FIG. 21) within the safety shield 92 with at least a portion of the end wall 92C within the safety shield 92 comprising a hard surface material. The safety shield 92 can include wear plates, or inserts, of a hard surface material that forms the end wall 92C. The hard surface material can comprise at least one of steel, hardened steel, high carbon steel, stainless steel, tungsten or the like.

Figure 18A:
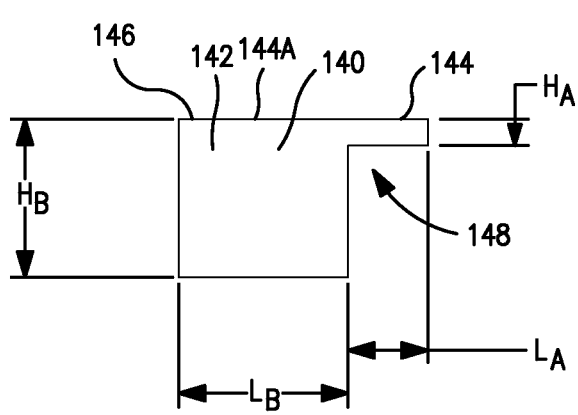
Figure 18A:
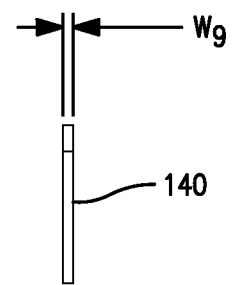
Figure 18A:
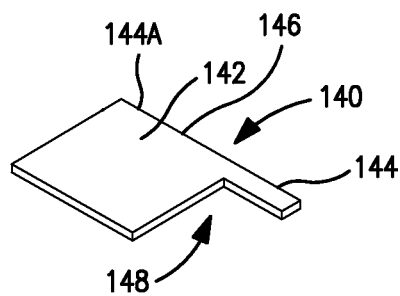
Figure 19:
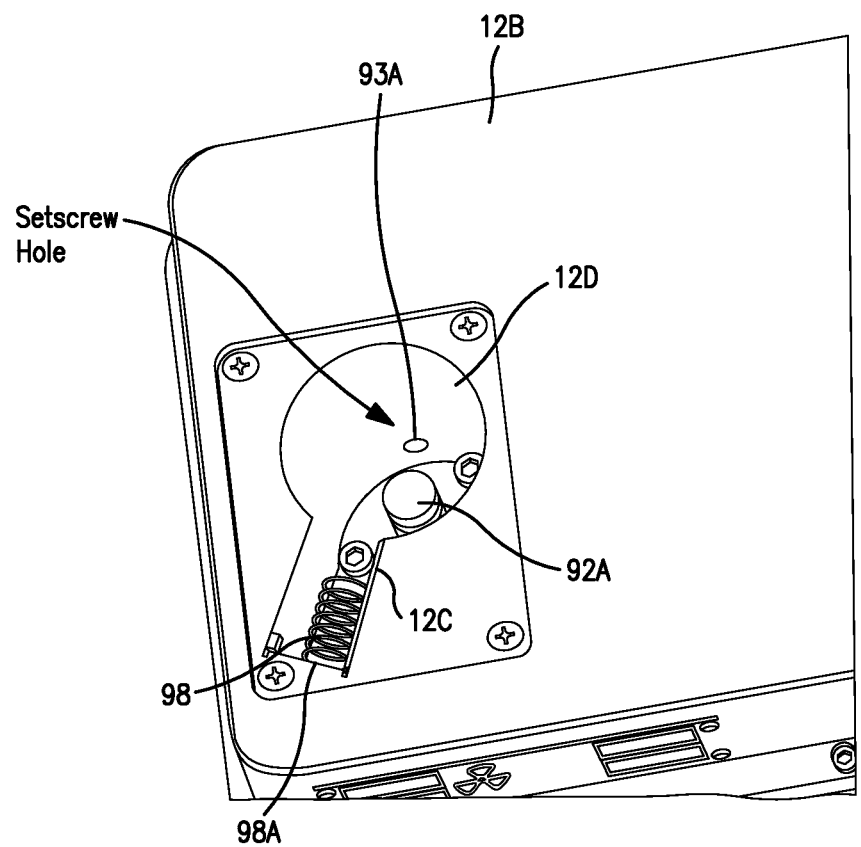
FIGS. 19-24 illustrate partially perspective bottom views of an embodiment of a nuclear gauge and components of a radiation shield assembly according to the present subject matter.
Figure 20:
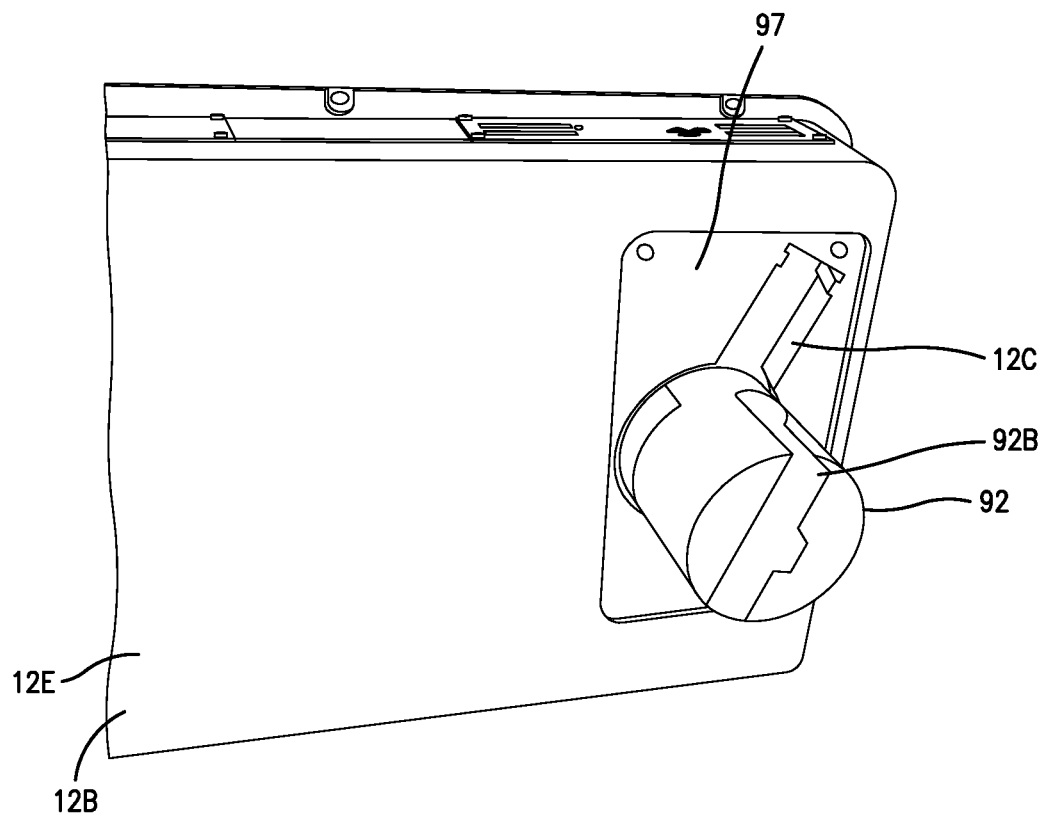

The at least one replaceable sliding guide 140 shown in FIGS. 18A-18C can be or can include a polymer having a low coefficient of friction. The polymer can be at least one of polytetrafluoroethylene, perfluoroalkoxy, and fluorinated ethylene propylene. The at least one replaceable sliding guide 140 can include a body 142 and an arm 144 extending outward from the body 142. The body 142 can include a rectangular shape with a base side 146 and the arm 144 can comprise a different rectangular shape extending from the base side 146, wherein the body 142 has a height that is larger than a height of the arm 144 thereby forming a notch 148 in the at least one replaceable sliding guide 140.

In such embodiments, the safety shield 92 can define an indentation 99, as shown in FIG. 17, configured to receive the arm 144 of the at least one replaceable sliding guide 140 so that an outer surface 140A of the at least one replaceable sliding guide 140 is about flush with an outer surface of shield track segment 92B of the safety shield 92. The arm 144 by engaging the indentation 99 can minimize rotation of the sliding guide 140 in the safety shield 92 caused by movement of the sliding block 94. In embodiments where the base 12B of the gauge housing 12 includes a base track segment 12C and the base track segment 12C and the shield track segment 92B are alignable to form the track 96, the base track segment 12C can have a width that is larger than the width of the shield track segment 92B for receiving the body 142 of the at least one replaceable sliding guide 140.

Figure 24:
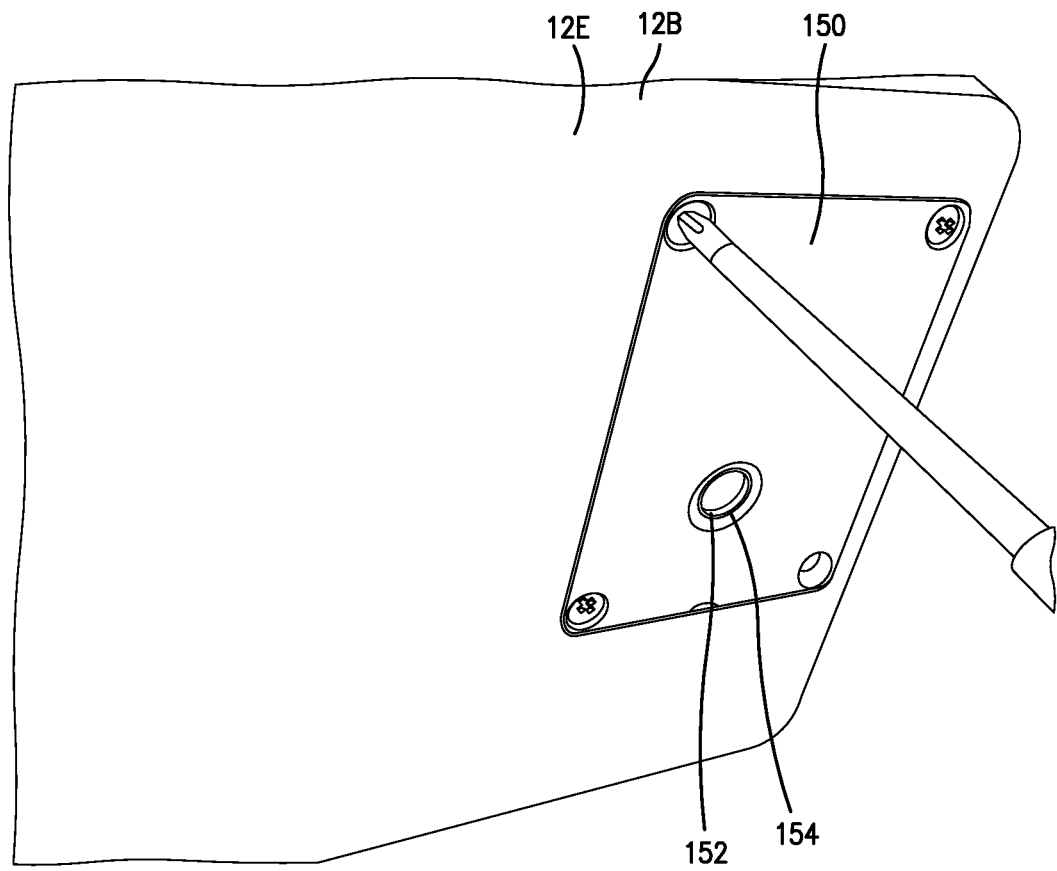
Figure 25A:
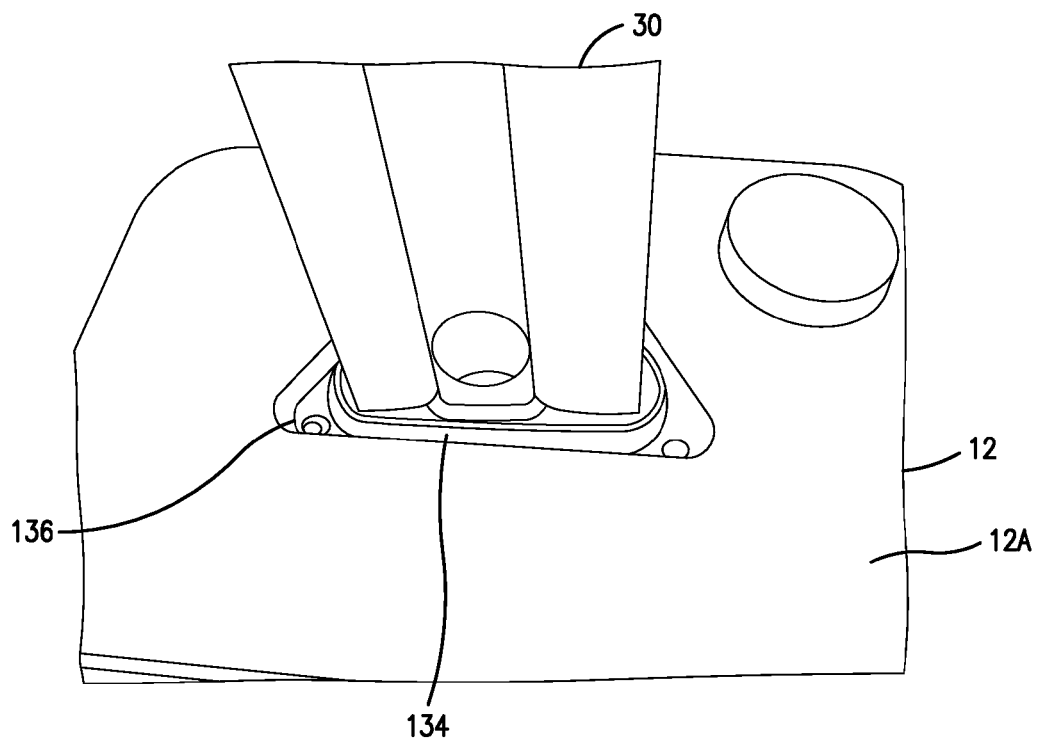
FIGS. 25A-25C illustrate partially perspective views of an embodiment of a nuclear gauge according to the present subject matter.
Figure 25B:
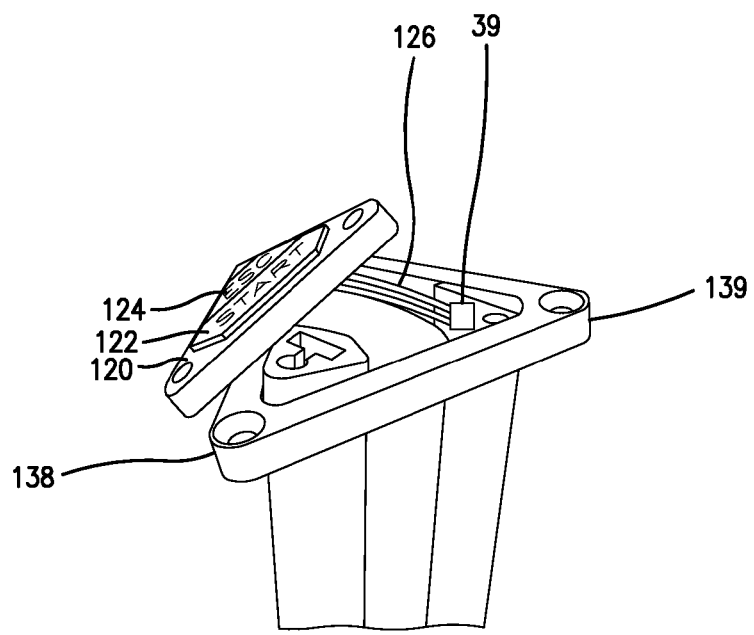
Figure 25C:
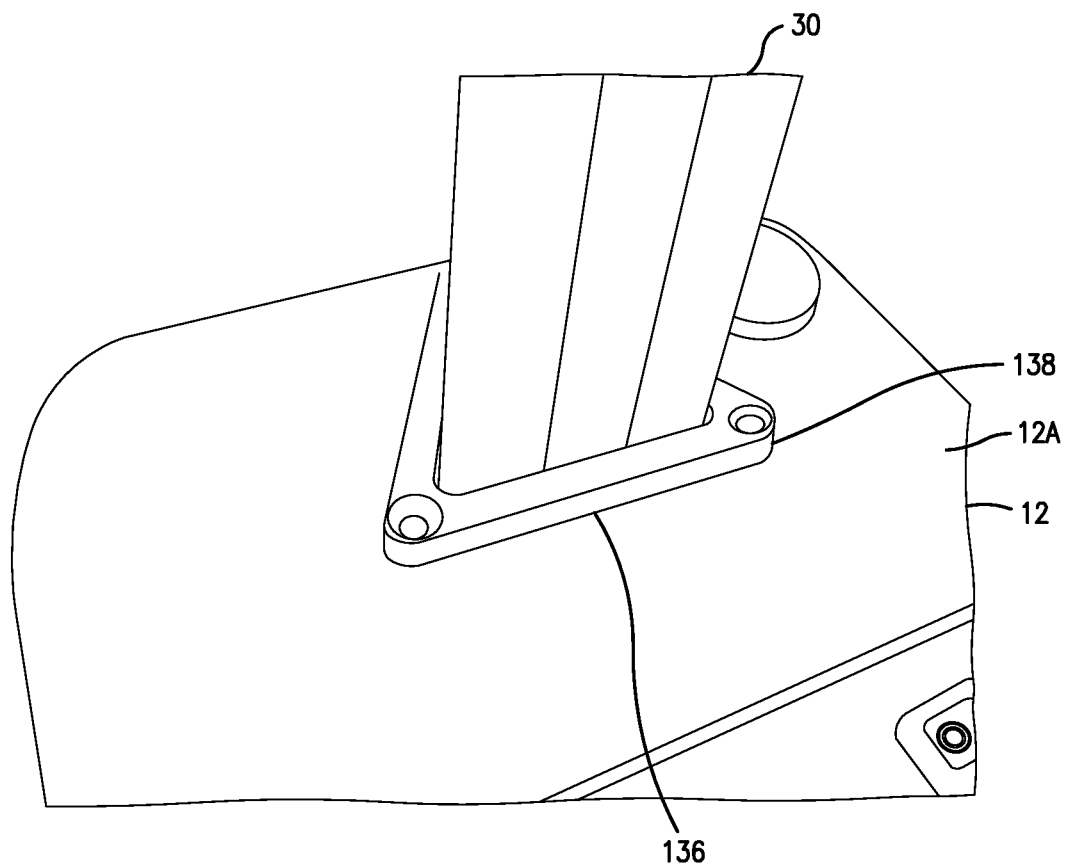

A cover plate 150 for securing the radiation shield assembly 90 within the gauge housing 12 can be included with the radiation shield assembly 90. The cover 150 can be a scraper plate that includes a scraper 152. The scraper ring 152 can be held in place in the cover plate 150 by a ring retainer 154 as shown in FIG. 24. The cover plate 150 can be placed in a recess 97 in the lower surface 12E of the base 12B of the gauge housing 12. Once installed, the cover plate 150 can abut the base side 144A of the at least one replaceable sliding guide 140. The outer surface of the cover plate 150 can be flush with the lower surface 12E of the base 12B. The cover plate 150 is positioned on the base 12B at an angle that covers the entire radiation shield assembly 90 and such that the rest of the radiation shield assembly 90 is contained inside the base 12B underneath the cover plate 150.

Referring back to the remote keypad 120 as shown in FIGS. 1-3 and 25B, such a keypad 120 located at the end of the tower 30 distal from the gauge housing 12 is intended to reduce the amount of bending and/or stooping required by the operator of the gauge 10. The operator's greatest benefit is gained while using the gauge 10 on an asphalt mat in the backscatter position. The operator will identify a measurement location on the asphalt mat. The operator will then move the source rod 20 to the backscatter position of approximately contacting the surface (the transmission mode assumes a BS position of zero, true that it is about 2 inches from safe position, but safe is not zero). The operator can then, with very little movement, press the start switch 122 to initiate the gauge counting. The location of the remote keypad 120 when located on the end of the tower 30 distal from the gauge housing 12 can be approximately two feet off of the asphalt mat and remains at that distance regardless of the source rod position.

Alternatively, the operator can identify the measurement location, place the source rod 20 in the backscatter position and then press a start switch on the user interface 13 of the gauge 12 located on the gauge housing 12. The location of the user interface 13 on the gauge housing 12 is approximately 5 to 6 inches off of the asphalt mat. Typically, to press the start switch on the user interface 13 located on the gauge housing 12 to initiate a gauge count, the operator will have to bend their back all of the way forward or stoop down closer to the asphalt mat to begin a gauge count. While the use of the remote keypad 120 provides a more ergonomically safe method to operate the gauge 10, either the remote keypad 120 or the user interface 13 on the gauge housing 12 can be used.

Thus, the first and second user interfaces 13 and 120 share some functionality with the first and second user interfaces with each including at least one keypad switch having functionality for communicating the same user input to the nuclear gauge computing system. For example, both the remote keypad 120 and the user interface 13 on the gauge housing can share the "start" and "escape" functions in the embodiment shown, since the remote keypad 120 includes both a start switch 122 and an escape switch 124. Electrically, the start switch 122 and escape switch 124 can be wired in parallel to the same two keys on the user interface 13 located on the gauge housing 12. The firmware operating the gauge 10 can be written in a manner that will allow a single key press of the start switch 122 to begin a gauge count and allow the operator to store that gauge count information in a gauge memory in the CPU 17 with an additional single key press of the start switch 122. Alternatively, an I/O interrupt could be initialed by start switch 122 letting the gauge software enter the requested state, such as starting a count or measurement.

The remote keypad 120 can be located on the stationary support tower 30. This tower 30 provides an excellent location for a stationary keypad and a routing compartment 39 to route electrical wiring 126 from the remote keypad 120 into the gauge housing 12 for connection with the CPU 17. Alternatively, the remote keypad 120 can be located on the handle 50. Because the handle 50 moves with the source rod 20, the power source to operate the remote keypad 120 could be contained within the handle 50. For example, a battery can be provided or power can be established with sliding contacts between the gauge 10 and handle 50.

Further, the keypad 120, as stated above, can be an entity totally separate from the physical body of the gauge 10. For example, the remote keypad 120 can be a fob that may be placed on a lanyard that can be hung around the operator's neck. Methods of communication between the CPU 17 in the gauge housing 12 and the remote keypad 120 for such embodiments where the remote keypad is secured to the handle or the remote keypad as a separate entity can be wireless in nature. For example, a transmitter can be located in the handle and a receiver can be located in the gauge housing for embodiments where the remote keypad is located on the handle. For embodiments where the remote keypad is a separate entity such as a fob, a transmitter can be located in the remote keypad and a receiver can be located in the gauge housing. Methods of wireless communications can be established via infrared or RF, BLUETOOTH®, or the like.

Methods of Assembly

The gauge 10 can be assembled in different ways including the tower 30, handle 50, and source rod 20 or related components. The methods of assembling a gauge and its related components set forth below are provided by way of example to illustrate embodiments thereof and are not meant to limit the present subject matter. Other methods of assembling a gauge and its related components can be used without deviating from the scope and spirit of the present subject matter.

As stated above, the tower 30 can be provided that has a vertical channel 34 therein in which a source rod 20 can reside. The vertical channel 34 can include an inlet 34A that extends along the side 30A of the tower 30 over the length of the vertical channel 34. The tower 30 can also include an indexing groove 36 that opens into the vertical channel 34. Further, the tower 30 can have a measurement compartment 38 and/or a routing compartment 39 disposed therein.

The index positioning strip 80 can be placed and secured in the indexing groove 36 of the tower 30. The bracket 72 can be inserted into the vertical channel and secured in the tower 30. For example, the bracket 72 can be secured in the indexing groove 36 of tower 30. During insertion of the bracket 72, the mid-portion 72C of the bracket 72 can pass through the slots 30D in the edges 30B of the tower 30 and the second end portion 72B resting within the grooves 30C in the edges 30B so that the bracket aperture 72D aligns with an axis of the vertical channel 34. The upper seal 74 can be inserted into the vertical channel 34 so as to reside against the underside of the bracket 72. The seal 74 can be slowly pressed into the vertical channel 34 of the tower 30 with the finger of an assembler or a tool until the seal 74 seats against the bracket 72.

The tube spacer 76 can be inserted into the vertical channel 34 so as to abut against the seal 74. The tube spacer can include one or more washers. For example, a top washer 76B can abut against the upper seal 74 when the tube spacer is inserted. A bottom washer 76C can be position to engage the source rod bearing 78. The tuber spacer 76 can retain grease to lubricate the movement of the source rod 20.

The source rod bearing 78 can be placed in the shield housing 12D of the base 12B of the housing 12 to align with the vertical cavity 14. A source rod bearing 78 can include a seal wiper 78A that is placed in a recess of the source rod bearing 78. The tower 30 can be carefully lowered onto the source rod bearing 78 with the tube spacer 76 engaging the source rod bearing 78. For example, the bottom washer 76B of the tube spacer 76 can engage the seal wiper 78A of the source rod bearing 78. When in position, the tower can be secured to the base 12B of the gauge housing 12 so that the vertical channel 34 of the tower 30 should align with the vertical cavity 14 of the base 12B of the gauge housing 12 to form the vertical conduit 32.

The depth strip 100 can be used to provide non-contact measurements used to determine the depth at which the source rod is positioned during use. The depth strip 100 can include Hall Effect sensors 102 that sense the magnetic field of a magnet 64 on the handle 50. The depth strip 100 can include a parting line 100A that allows the depth strip 100 to be used as an 8-inch unit or a 12-inch unit. Another parting line can be included on the depth strip to create a depth strip that can be used in a backscatter only gauge. For 8-inch units, the depth strip 100 can be parted at this parting line 100A. When not parted, the whole depth strip 100 can be used for 12-inch units. The depth strip 100 can include wiring 106 that can be use to connect it to the CPU 17 and/or power source of the gauge 10.

Figure 12:
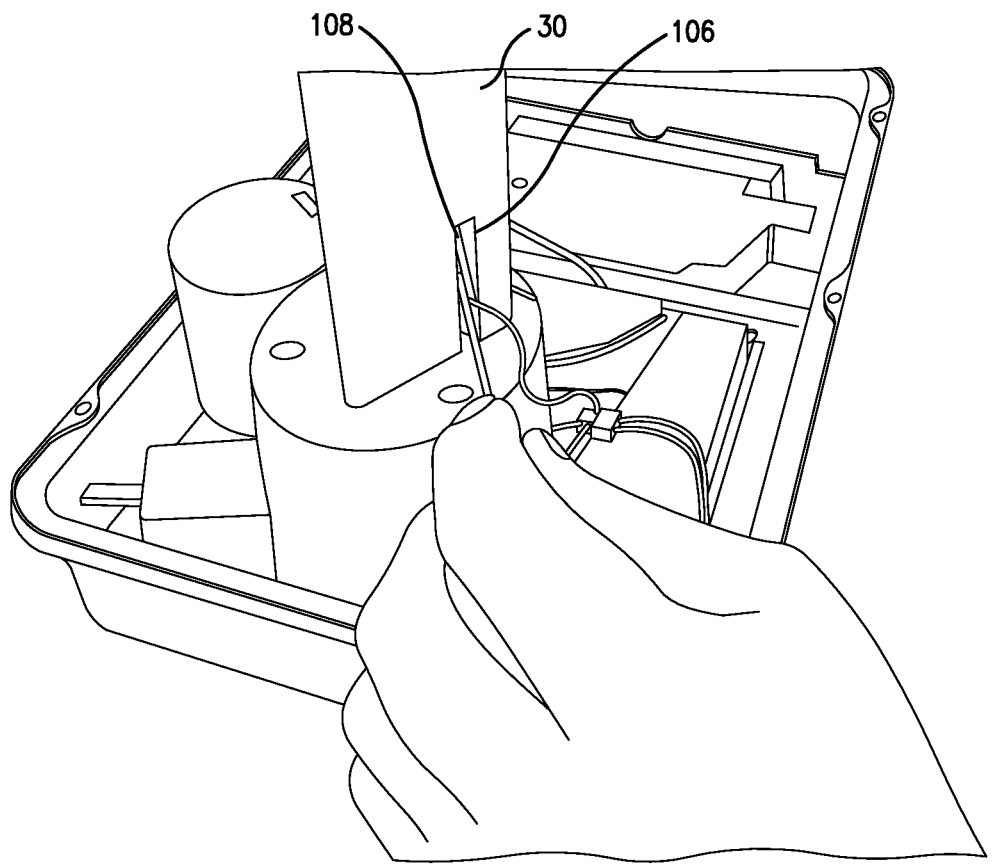
FIG. 12 illustrates a perspective view of an embodiment of a support tower and base of a gauge housing according to the present subject matter.

Before the attachment of the tower 30 to the base 12B of the gauge housing 12, the depth strip 100 can be inserted into the measurement compartment 38 of the tower 30 so that the depth strip is in the proper location to determine the source rod locations based on the position of the indexing holes 82 of the index positioning strip 80. If the compartment 39 is a passageway, the depth strip 100 can be inserted into the measurement compartment at the bottom of the tower 30 so that the top of depth strip 100 extends through the top of the tower 30. A placement pin 100B can be inserted into an aperture 100C in the depth strip 100. After the insertion of the pin 100B, the depth strip 100 can be pushed back into the tower 30 so that the pin 100B engages the top of the tower 30 so that the Hall Effect sensors 102 align with the index holes 82 of the index positioning strip 80. For example, the tower can include a seat that receives the pin 100B. After insertion, the integrated circuits, or Hall Effect sensors, 102 of the printed circuit board 104 of the depth strip 100 should face the vertical channel 34 where the source rod 100 will reside after insertion into the tower 30. The tower 30 can include a wiring aperture 108 through which the wiring 106 can be pulled as shown in FIG. 12. The wiring 106 can then be properly connected to the gauge 10.

A handle 50 having a grip portion 50A, an engagement portion 50B, and a neck portion 50C can be provided. A plunger 56 can be inserted into a plunger aperture 56B that can extend through the engagement portion 50B and neck portion 50C and into the grip portion 50A of the handle 50. The plunger 56 can be checked to ensure that it fits properly without any binding.

Before insertion of the plunger 56, a spring 60 can be inserted into the plunger aperture 56B. A lubricant can be applied to the spring 60 before insertion of the spring 60 into the plunger aperture 56B. The plunger 56 can also be lightly greased or lubricated at its back end. When inserted, the plunger 56 should be oriented so that the one or more retraction grooves 56A will be oriented for receipt of a corresponding protrusion 58E on the trigger 58. Further the clearance hole 68 in the plunger 56 should be alignable with the clearance hole 66 in the engagement portion 50C. Any excess lubricant can be wiped off the handle 50 after insertion of the plunger 56.

For installation of the trigger 58 into the grip portion 50C, a pivot pin 58A can be driven into a pivot aperture 53A located in the grip portion 50A of the handle 50 at the end distal from the neck portion 50C. The pivot pin 58A can be driven into the pivot aperture using, for example, a hammer and tap. The trigger spring 59 can be placed on the trigger 58 close to the end that is distal from the pivot groove 58C. Lubricant can be applied to the one or more protrusions 58E to reduce friction when the one or more protrusions 58E engage the corresponding retraction grooves 56A. For example, lubricant can be liberally applied to the one or more protrusions 58E using a brush as shown.

The trigger 58 can now be installed into the handle 50. The pivot groove 58C of the trigger 58 can engage the pivot pin 58A inserted into the grip portion 50A of the handle 50. The trigger 58 can then be placed in the trigger cavity 53B with the trigger spring 59 facing inside of the handle 50. The trigger 58 can then be pressed into the handle 50 so that the one or more protrusions 58E enter a protrusion cavity 53D shown in FIG. 13B and engage the corresponding one or more retraction grooves 56A. The locking pin 58B can then be inserted through the locking aperture 53C that extends through the engagement portion 50B and neck portion 50C into the handle cavity 53B, while the trigger 58 is pressed into the handle cavity 53B. The locking pin 58B can be driven to the correct depth so as to engage the slot 58D in the end of the trigger 58 proximate to the neck portion 50C and distal from the pivot groove 58C. The locking pin 58B can be driven to a point where it does not block the clearance hole 66 or the threaded section 52A in the engagement portion 50B. The locking pin 58B can be driven into the handle 50, for example, by a hammer and a thin long nail driver until it passes through the lower threaded section 52A where the source rod 20 will be engaged so that the source rod 20 can be screwed into the engagement portion 50B without any interference but not so deep as to interfere with the movement of the trigger 58. In this manner, the trigger 58 is locked into the grip portion 50A of the handle 50.

For embodiments that use Hall Effect sensors in the depth strip, the magnet 64 can be inserted into the recess 53E (shown in FIG. 13C) in the handle 50. The one or more slider discs 51A, 51B can also be installed onto the engagement portion 50B. For example, the top slider disc 51A can be inserted into the top of the engagement portion 50B in the clearance hole 66 and secured in place by a set screw 69A. The slider discs 51A can have an aperture 68A that aligns with the clearance hole 66 to provide access to the fine adjustment mechanism 54. The bottom slider disc 51B can be secured in an annular groove at the base of the engagement portion 50B. The set screw 69 can be partially screwed into the handle 50. After properly setting the source height of the source rod 20, the set screw 69 can be properly tightened and secured to secure the source rod 20 in place.

Once the handle 50 is assembled, the source rod 20 can be affixed to the handle 50. The fine adjustment mechanism 54 can be secured to the source rod 20. For example, the screw 54A can be screwed into the screw hole 54B in the source rod 20 and then secured.

The source rod 20 can be secured to the handle 50 and adjusted to a proximate source height by the coarse adjustment mechanism 52. For example, the end of the source rod 20 that is distal from the source 22 can be inserted into the threaded section 52A of the engagement portion 50B of the handle 50. When initially screwing the source rod 20 into the handle, the threaded section 52A can operate as the coarse adjustment mechanism 52. Handle 50 can be screwed onto the source rod 20 until a specified distance of the threads 20A remains visible. For example, a distance of thread visible can be between about 0.25 inches and about 0.5 inches, for instance, about 0.44 inches. The fine adjustment mechanism 54 in the form of the screw 54A should align with the clearance hole 66 of the engagement portion and when the plunger 56 is extended, with the clearance hole 68 of the plunger 56.

To incrementally adjust the height of the source rod 20, the handle 50 that is holding the source rod 20 can be inserted into the vertical channel of the tower 30. The handle 50 is set to a backscatter position. A screwdriver or wrench can be inserted through the clearance holes 66 and 68 to engage the screw 54A for adjusting the source rod movement up or down inside the handle 50. The screwdriver or wrench is turned to finely tune the height of the source rod 20. Once the source rod has the proper source height, the set screw 69 can be tightened and secured.

For example, to correctly measure the height of the source rod 20, a depth gauge can be inserted through the opening in scraper plate 150 for source height setting. For instance, the depth gauge can be set to a zero position. The depth gauge can then be inserted through the bottom scraper plate 150 and can measure the distance to the tip of the source rod 20. The measurement is read from the tip of the source rod 20 to the lower surface of the base 12B of the gauge housing 12. The proper setting of the source height as measured from the lower surface of the base 12B can vary depending on the type of gauge. For example, the proper setting distance can range from about −0.010 inches +/− about 0.005 of an inch to about −0.203 inches +/− about 0.005 of an inch. Some gauges can have a proper setting distance of −0.137 inches +/− about 0.005 of an inch. If a proper distance is not the specified, then a setting of −0.010 inches +/− about 0.005 of an inch can be used. If the measurement taken by the depth gauge is not correct, then the screw 54A can be incrementally turned in partial or full rotations to move the source rod 20 to the correct position. Once the correct source height is obtained by the source rod 20, the set screw 69 can be tightened and secured.

Embodiments of the present disclosure shown in the drawings and described above are exemplary of numerous embodiments that can be made within the scope of the appending claims. It is contemplated that the configurations of nuclear gauges, their components and the methods of assembling the same can comprise numerous configurations other than those specifically disclosed. The scope of a patent issuing from this disclosure will be defined by these appending claims.

What is claimed is:

1. A nuclear gauge suitable for measuring the density and/or moisture of material, comprising:
   a gauge housing having a vertical cavity therethrough;
   at least one radiation detector located within the housing;
   a tower defining a vertical channel therein, the tower disposed on the gauge housing with the channel aligned with the cavity to form a vertical conduit;
   a vertically moveable source rod extending within the conduit;
   a radiation source operatively positioned within a distal end of the source rod;
   a handle secured to the source rod for vertically extending and retracting the source rod to a plurality of predetermined source rod locations so as to change the spatial relationship between the radiation source and the at least one radiation detector, the handle providing a fine adjustment element for adjusting the height of the source rod for positioning the radiation source relative to the at least one radiation detector to provide proper measurements at the different predetermined source rod locations; and
   wherein the handle further comprises a coarse adjustment mechanism that works in conjunction with the fine adjustment element for adjusting the height of the source rod for positioning the radiation source relative to the at least one radiation detector to provide proper measurements at the different predetermined source rod locations.

2. A nuclear gauge according to claim 1, wherein the gauge housing comprises a top cover and a base with the base having the vertical cavity therethrough.

3. A nuclear gauge according to claim 2, further comprising an O-ring positionable in a groove within the base of the gauge housing between the base and the cover.

4. A nuclear gauge according to claim 1, wherein the handle further comprises a plunger and a trigger, the plunger extendable to engage notches disposed within the tower and retractable to disengage the notches by actuation of the trigger.

5. A nuclear gauge according to claim 4, further comprising an index positioning strip having index holes therein, the index positioning strip securable at a designated location within the vertical channel of the tower.

6. A nuclear gauge according to claim 4, wherein the handle defines an adjustment aperture therein to permit access to the fine adjustment element.

7. A nuclear gauge according to claim 4, wherein the plunger defines an alignment aperture that aligns with the adjustment aperture in the handle when the plunger resides in an extended position.

8. A nuclear gauge according to claim 1, wherein the coarse adjustment mechanism includes a threaded section within the handle.

9. A nuclear gauge according to claim 8, wherein the fine adjustment element includes a screw.

10. A nuclear gauge according to claim 9, wherein the screw is securely affixed to the source rod such that the screw does not rotate separately from the source rod.

11. A nuclear gauge according to claim 1, wherein the fine adjustment element permits adjustment of the source rod to plus or minus about 0.005 inch.

12. A nuclear gauge according to claim 1, wherein the fine adjustment element permits adjustment of the source rod to plus or minus about 0.0001 inch.

13. A nuclear gauge according to claim 1, wherein the source rod is securely held in place after the height of the source rod is adjusted the fine adjustment element.

14. A nuclear gauge according to claim 1, wherein the handle further comprises a set screw for holding and locking the source rod in place after the height of the source rod is adjusted with the fine adjustment element.

15. A nuclear gauge according to claim 1, wherein the source rod is in a backscatter position when the height of the source rod is adjusted with the fine adjustment element.

16. A nuclear gauge according to claim 1, wherein the tower comprises a top and a lower end and comprising a remote keypad located on the top end of the tower distal from the gauge housing.

17. A nuclear gauge according to claim 16, wherein the remote keypad comprises a plurality of switches.

18. A nuclear gauge according to claim 17, wherein the plurality of switches comprise a start switch and an escape switch.

19. A nuclear gauge according to claim 16, wherein the tower includes a routing compartment for routing the electrical wiring for the keypad into the gauge housing.

20. The nuclear gauge of claim 1, wherein the nuclear gauge is a density gauge, a bulk density gauge, a thin overlay gauge, a thin layer gauge, or a combination thereof.

21. The nuclear gauge of claim 1, wherein the at least one radiation detector is selected from a group consisting of Gieger-Müller tubes, proportional counters or Neutron tubes.

22. The nuclear gauge of claim 1, further comprising a moisture detector.

23. A nuclear gauge suitable for measuring the density and/or moisture of material, comprising:
   a gauge housing having a vertical cavity therethrough;
   at least one radiation detector located within the housing;
   a tower defining a vertical channel therein, the tower disposed on the gauge housing with the channel aligned with the cavity to form a vertical conduit;
   a vertically moveable source rod extending within the conduit;
   a radiation source operatively positioned within a distal end of the source rod;
   a handle secured to the source rod for vertically extending and retracting the source rod to a plurality of predetermined source rod locations so as to change the spatial relationship between the radiation source and the at least one radiation detector, the handle providing a fine adjustment element for adjusting the height of the source rod for positioning the radiation source relative to the at least one radiation detector to provide proper measurements at the different predetermined source rod locations;
   wherein the gauge housing comprises a top cover and a base with the base having the vertical cavity therethrough;
   further comprising an O-ring positionable in a groove within the base of the gauge housing between the base and the cover; and
   wherein the tower has a triangular cross-section.

24. A nuclear gauge according to claim 23, further comprising an O-ring having a diameter which fits tightly around the triangular cross-section of the tower and a triangular trim plate having an outer lip that pushes the O-ring against the tower to create a water resistant seal.

25. A nuclear gauge suitable for measuring the density and/or moisture of material, comprising:
- a gauge housing having a vertical cavity therethrough;
- at least one radiation detector located within the housing;
- a tower defining a vertical channel therein, the tower disposed on the gauge housing with the channel aligned with the cavity to form a vertical conduit;
- a vertically moveable source rod extending within the conduit;
- a radiation source operatively positioned within a distal end of the source rod;
- a handle secured to the source rod for vertically extending and retracting the source rod to a plurality of predetermined source rod locations so as to change the spatial relationship between the radiation source and the at least one radiation detector, the handle providing a fine adjustment element for adjusting the height of the source rod for positioning the radiation source relative to the at least one radiation detector to provide proper measurements at the different predetermined source rod locations;
- wherein the handle further comprises a plunger and a trigger, the plunger extendable to engage notches disposed within the tower and retractable to disengage the notches by actuation of the trigger;
- further comprising an index positioning strip having index holes therein, the index positioning strip securable at a designated location within the vertical channel of the tower; and
- further comprising a depth strip positionable in the tower, the depth strip having Hall Effect sensors therein that are alignable with the index holes of the index positioning strip, wherein the handle having a magnet thereon that is detectable by the hall effect sensors to provide non-contact measuring of the positioning of the source rod.

26. A nuclear gauge according to claim 25, wherein the depth strip includes a parting line with the depth strip being convertible from a 12-inch unit to an 8-inch unit along the parting line.

27. A nuclear gauge according to claim 25, wherein the tower includes a measurement compartment for housing the depth strip.

28. The nuclear gauge of claim 25, wherein the depth strip includes a second parting line that permits the depth strip to be convertible into a unit that is useable in backscatter only gauges.

29. A nuclear gauge according to claim 25, wherein the index positioning strip is adjustable within the tower.

30. A source rod assembly for use in a nuclear gauge, the source rod assembly comprising:
- a vertically moveable source rod;
- a radiation source operatively positioned within a distal end of the source rod; and
- a handle secured to the source rod for vertically extending and retracting the source rod to a plurality of predetermined source rod locations so as to change the spatial relationship between the radiation source and the at least one radiation detector, the handle providing a fine adjustment element for adjusting the height of the source rod for positioning the radiation source relative to the at least one radiation detector to provide proper measurements at the different predetermined source rod locations; and
- wherein the handle further comprises a coarse adjustment mechanism that works in conjunction with the fine adjustment element for adjusting the height of the source rod for positioning the radiation source relative to the at least one radiation detector to provide proper measurements at the different predetermined source rod locations.

31. A source rod assembly according to claim 30, comprising a tower defining a vertical channel for the source rod, wherein the handle further comprises a plunger and a trigger, the plunger extendable to engage notches disposed within the tower and retractable to disengage the notches by actuation of the trigger.

32. A source rod assembly according to claim 31, wherein the handle defines an adjustment aperture therein to permit access to the fine adjustment element.

33. A source rod assembly according to claim 32, wherein the plunger defines an alignment aperture that aligns with the adjustment aperture in the handle when the plunger resides in an extended position.

34. A source rod assembly according to claim 30, wherein the coarse adjustment mechanism includes a threaded section within the handle.

35. A source rod assembly according to claim 34, wherein the fine adjustment element includes a screw.

36. A source rod assembly according to claim 35, wherein the screw is securely affixed to the source rod such that the screw does not rotate separately from the source rod.

37. A source rod assembly according to claim 30, wherein the fine adjustment element permits adjustment of the source rod to plus or minus about 0.005 inch.

38. A source rod assembly according to claim 30, wherein the fine adjustment element permits adjustment of the source rod to plus or minus about 0.0001 inch.

39. A nuclear gauge comprising:
- a gauge housing including a vertical cavity therethrough and a base;
- a radiation detector located within the gauge housing and adjacent to the base of the gauge housing;
- a source rod housing including an interior and first and second ends, the first end being attached to the base of the gauge housing, the second end being distal from the first end and the base;
- a vertically movable source rod being positioned in the interior of the source rod housing and extending into the cavity of the gauge housing;
- a radiation source operatively positioned within a distal end of the source rod;
- a computing system located within the gauge housing;
- a user interface in communication with the computing system and attached to the second end of the source rod housing, wherein the user interface comprises a keypad having a start switch for initiating a gauge count and an escape switch for aborting a gauge count;
- a handle coupled to the source rod;
- wherein the handle further comprises a plunger and a trigger, the plunger extendable to engage notches disposed within the source rod housing and retractable to disengage the notches by actuation of the trigger, and
- wherein the handle further comprises an adjustment element separate from the notches and the plunger for calibrating the height of the source rod when the plunger engages one of the notches.

40. The nuclear gauge according to claim 39, wherein the computing system includes a memory for storing the results of the gauge count.

41. The nuclear gauge according to claim 39, wherein the user interface and the computing system are adapted for wireless communication.

42. The nuclear gauge according to claim 39, comprising a wire line adapted for communicatively connecting the user interface and the computing system.

43. The nuclear gauge according to claim 39, comprising a wireless communications system adapted for communicatively connecting the user interface and the computing system via a wireless communications connection.

44. The nuclear gauge according to claim 39, wherein the user interface is a first user interface, and wherein the nuclear gauge comprises a second interface attached to the gauge housing and positioned a predetermined distance from the first user interface.

45. The nuclear gauge according to claim 44, wherein the first and second user interfaces share at least a portion of their functionality.

46. The nuclear gauge according to claim 44, wherein the first and second user interfaces each include at least one keypad switch having functionality for communicating the same user input to the computing system.

47. The nuclear gauge according to claim 39, wherein the nuclear gauge is a density gauge, a bulk density gauge, a thin overlay gauge, a thin layer gauge, or a combination thereof.

48. A nuclear gauge comprising:
   a gauge housing including a vertical cavity therethrough and a base;
   a radiation detector located within the gauge housing and adjacent to the base of the gauge housing;
   a source rod housing including an interior and first and second ends, the first end being attached to the base of the gauge housing, the second end being distal from the first end and the base;
   a vertically movable source rod being positioned in the interior of the source rod housing and extending into the cavity of the gauge housing;
   a radiation source operatively positioned within a distal end of the source rod;
   a computing system located within the gauge housing;
   a user interface in communication with the computing system and attached to the second end of the source rod housing, wherein the user interface comprises a keypad having a start switch for initiating a gauge count and an escape switch for aborting a gauge count; and
   a handle coupled to the source rod wherein the handle comprises a fine adjustment element and a coarse adjustment mechanism that works in conjunction with the fine adjustment element for adjusting the height of the source rod for positioning the radiation source relative to the radiation detector to provide proper measurements at different predetermined source rod locations.

* * * * *